(12) United States Patent
Woehr et al.

(10) Patent No.: US 6,287,278 B1
(45) Date of Patent: Sep. 11, 2001

(54) SPRING DIP SAFETY IV CATHETER

(75) Inventors: Kevin Woehr, Felsberg; Manfred Orth, Kassel, both of (DE); Mark Wynkoop, Coopersberg; Matthew Kohler, E. Greenville, both of PA (US)

(73) Assignee: B. Braun Melsungen, AG, Melsungen (DE)

( * ) Notice: Subject to any disclaimer, the term of this patent is extended or adjusted under 35 U.S.C. 154(b) by 0 days.

(21) Appl. No.: 09/183,697

(22) Filed: Oct. 30, 1998

Related U.S. Application Data

(63) Continuation-in-part of application No. 09/097,170, filed on Jun. 12, 1998, which is a continuation-in-part of application No. 08/915,148, filed on Aug. 20, 1997.

(51) Int. Cl.⁷ .................................................. A61M 5/00
(52) U.S. Cl. ........................................... 604/110; 604/263
(58) Field of Search ................................... 604/164–167, 604/110, 263, 167.01, 167.06

(56) References Cited

U.S. PATENT DOCUMENTS

| | | |
|---|---|---|
| 3,610,240 | 10/1971 | Harautuneian . |
| 3,904,033 | 9/1975 | Haerr . |
| 4,160,450 | 7/1979 | Doherty . |
| 4,725,267 | 2/1988 | Vaillancourt . |
| 4,735,618 | 4/1988 | Hagen . |
| 4,747,831 | 5/1988 | Kulli . |
| 4,795,432 | 1/1989 | Karczmer . |
| 4,846,809 | 7/1989 | Sims . |
| 4,929,241 * | 5/1990 | Kulli .................................... 604/263 |
| 4,944,725 | 7/1990 | McDonald . |
| 4,952,207 | 8/1990 | Lemieux . |
| 4,964,854 | 10/1990 | Luther . |
| 4,978,344 | 12/1990 | Dombrowski et al. . |
| 4,994,041 | 2/1991 | Dombrowski et al. . |
| 5,049,136 | 9/1991 | Johnson . |
| 5,051,109 | 9/1991 | Simon . |
| 5,053,017 * | 10/1991 | Chamuel .............................. 604/192 |
| 5,085,648 | 2/1992 | Purdy et al. . |
| 5,126,090 | 6/1992 | Egolf et al. . |
| 5,135,504 * | 8/1992 | McLees ............................... 604/164 |
| 5,147,327 | 9/1992 | Johnson . |
| 5,171,229 | 12/1992 | McNeil et al. . |
| 5,183,468 | 2/1993 | McLees . |
| 5,215,528 | 6/1993 | Purdy et al. . |
| 5,279,591 * | 1/1994 | Simon .................................. 604/263 |
| 5,300,045 * | 4/1994 | Plassche, Jr. ......................... 604/263 |
| 5,322,517 | 6/1994 | Sircom et al. . |
| 5,328,482 | 7/1994 | Sircom et al. . |

(List continued on next page.)

FOREIGN PATENT DOCUMENTS

WO9742989A1    11/1997   (WO) .............................. A61M/5/00

* cited by examiner

Primary Examiner—Anhtuan T. Nguyen
Assistant Examiner—Kevin C. Sirmons
(74) Attorney, Agent, or Firm—Christie, Parker & Hale, LLP

(57) ABSTRACT

A safety IV catheter includes a unitary, resilient needle guard received in a catheter hub. The needle guard includes a proximal arm or wall that includes an opening through which a needle passes for axial movement. When the needle is retracted from the catheter it releases the force that had previously prevented movement of the needle guard within the catheter hub. This in turn causes the needle guard to snap into a position in which it is clamped onto the needle shaft and in which its distal wall blocks access to the needle tip. In this condition, the spring needle guard and needle can be removed from the catheter hub. A slot or bulge may be formed in the needle shaft that engages with the needle guard after the protected needle and needle guard are removed from the catheter hub, thereby to prevent removal of the protected needle from the needle guard.

112 Claims, 13 Drawing Sheets

U.S. PATENT DOCUMENTS

| | | |
|---|---|---|
| 5,334,158 | 8/1994 | McLees . |
| 5,344,408 * | 9/1994 | Partika .................................. 604/192 |
| 5,370,623 | 12/1994 | Kreamer . |
| 5,423,766 | 6/1995 | Di Cesare . |
| 5,501,675 | 3/1996 | Erskine . |
| 5,558,651 | 9/1996 | Crawford et al. . |
| 5,584,809 | 12/1996 | Gaba . |
| 5,584,810 | 12/1996 | Brimhall . |
| 5,584,818 | 12/1996 | Morrison . |
| 5,599,310 | 2/1997 | Bogert . |
| 5,601,536 | 2/1997 | Crawford et al. . |
| 5,611,781 | 3/1997 | Sircom et al. . |
| 5,662,610 | 9/1997 | Sircom et al. . |
| 5,697,907 | 12/1997 | Gaba . |
| 5,718,688 | 2/1998 | Wozencroft . |
| 5,738,665 | 4/1998 | Caizza et al. . |
| 5,879,337 | 3/1999 | Kuracina et al. .................... 604/192 |
| 6,001,080 | 12/1999 | Kuracina et al. .................... 604/171 |

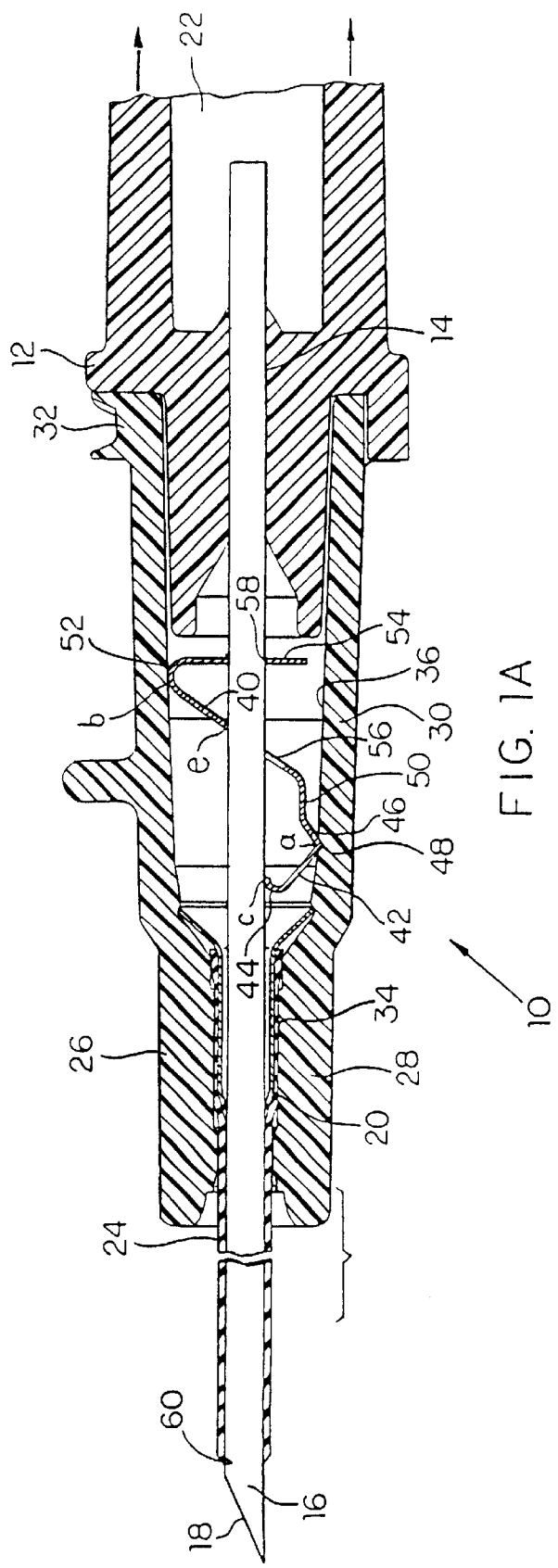
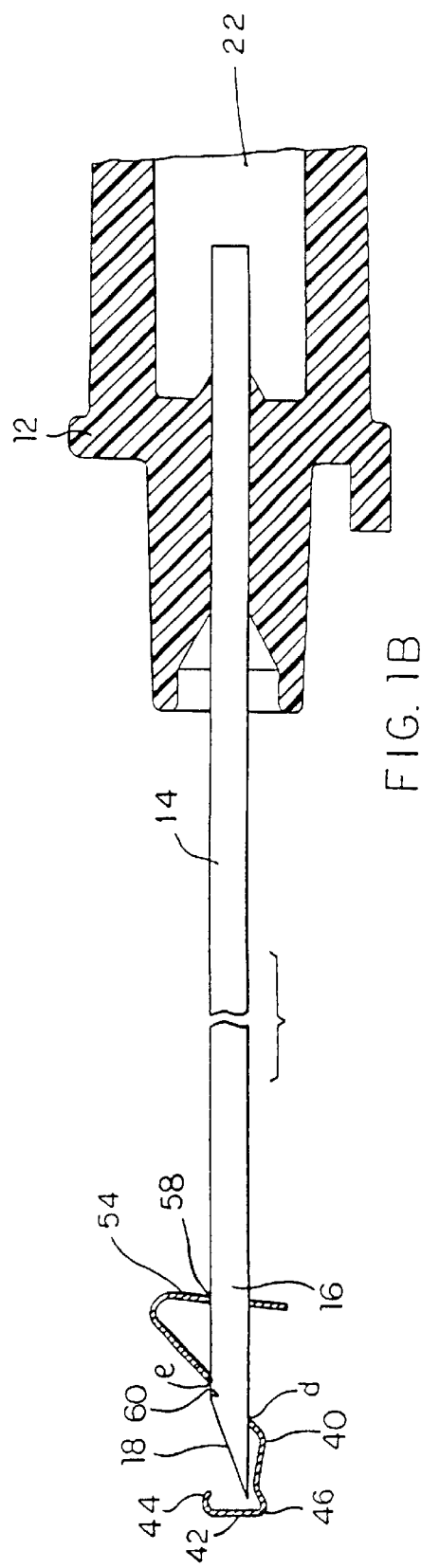
FIG. 1A
FIG. 1B

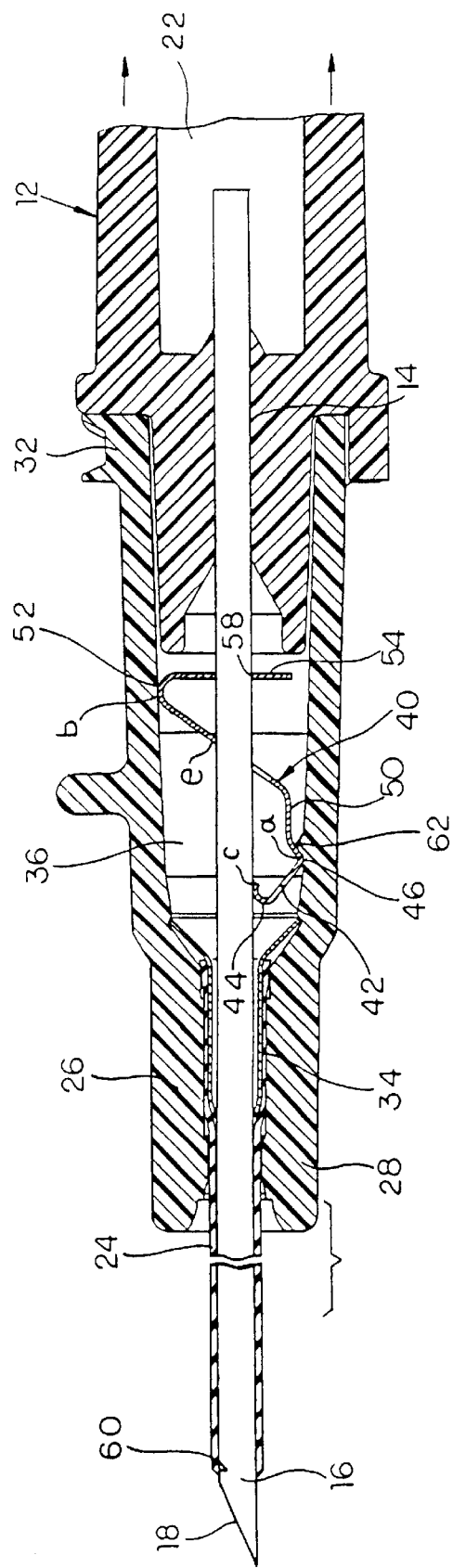
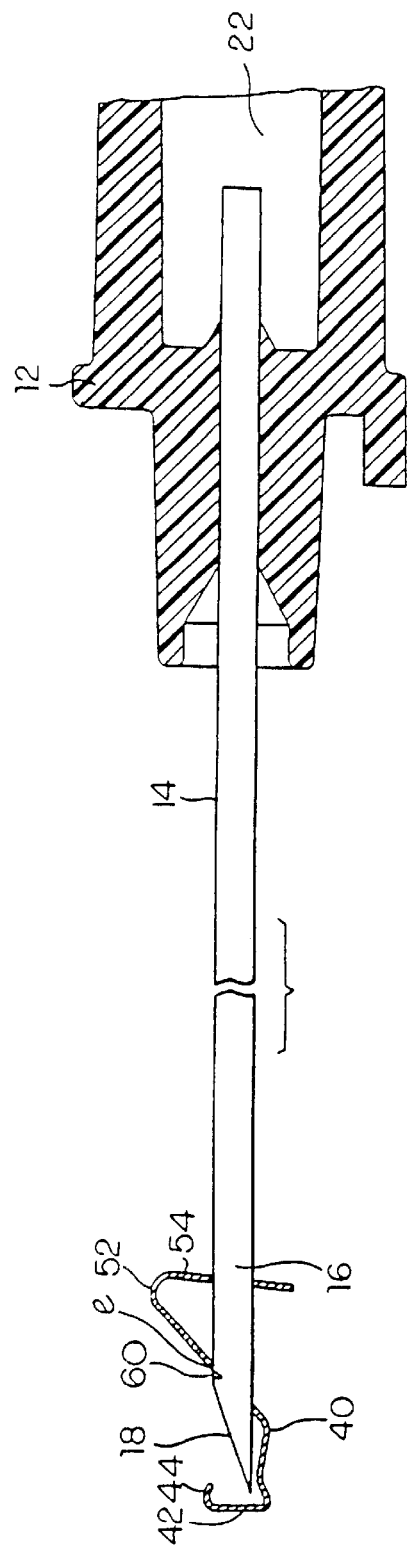
FIG. 2A
FIG. 2B

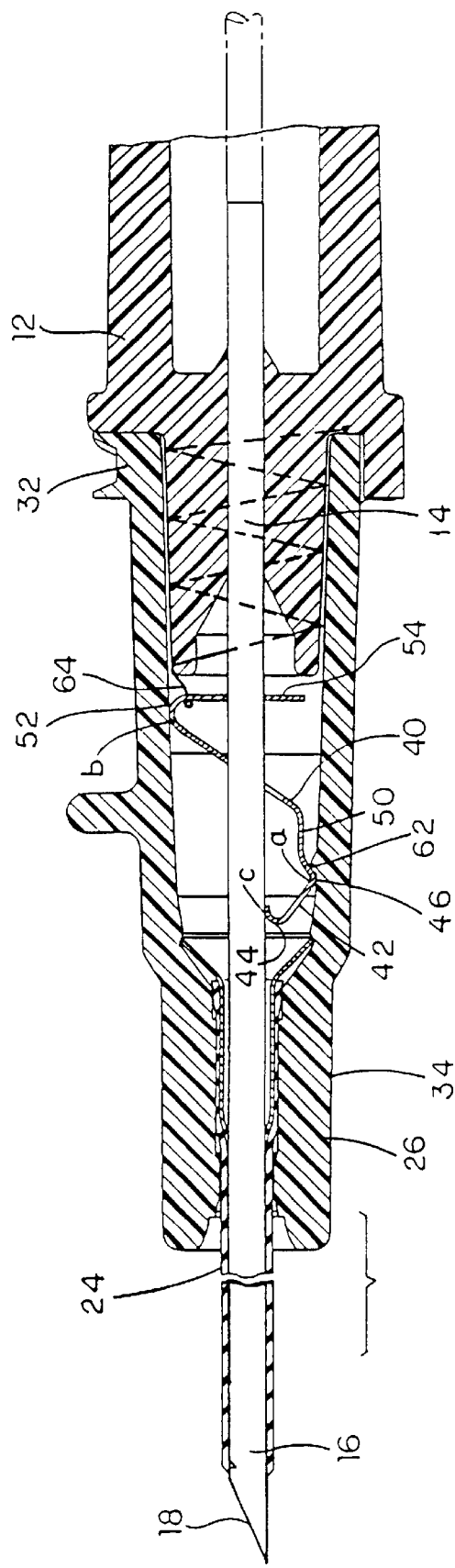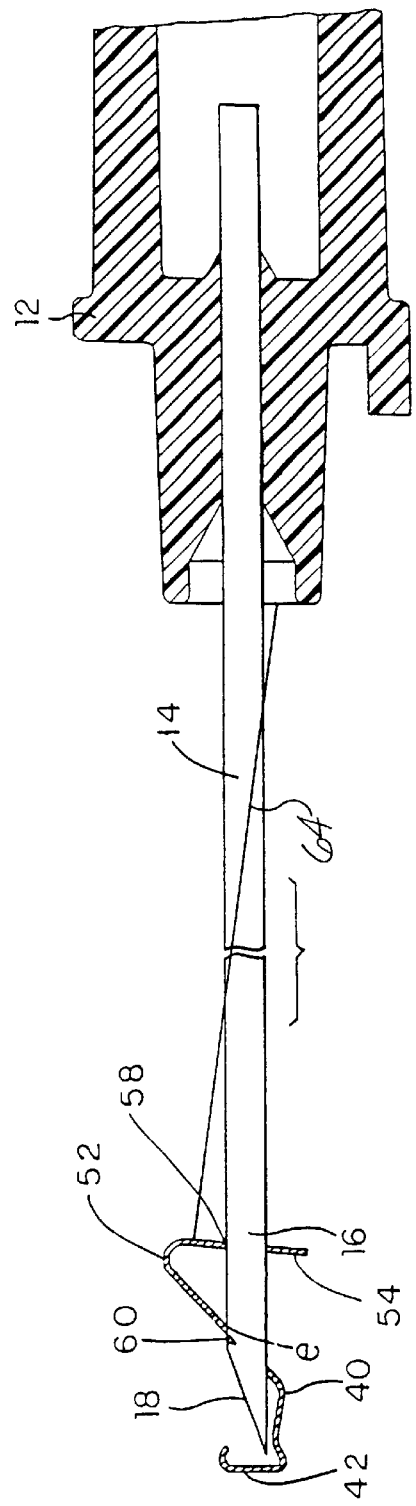
FIG. 3A
FIG. 3B

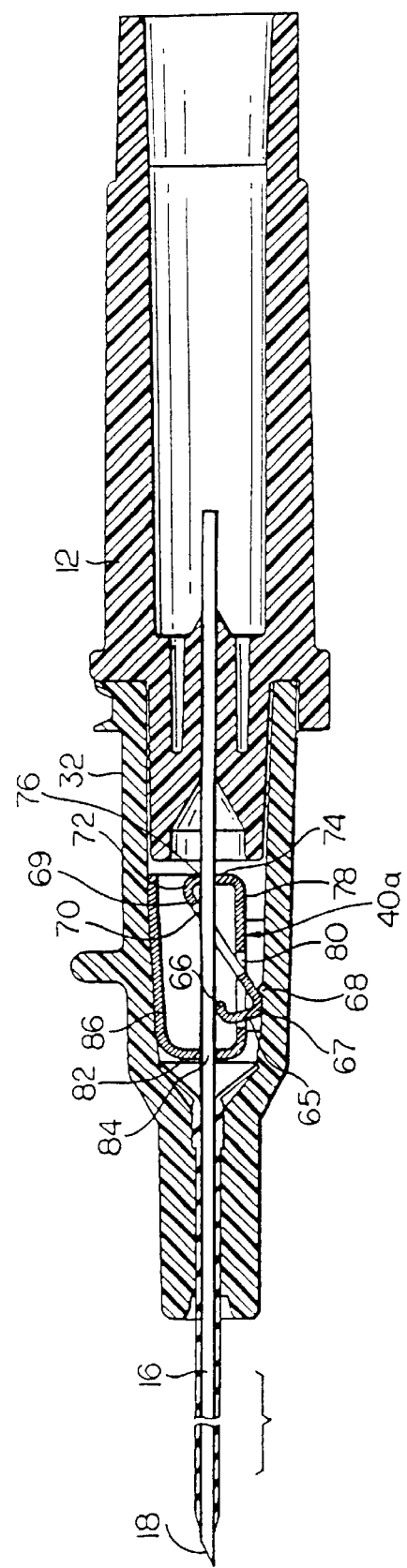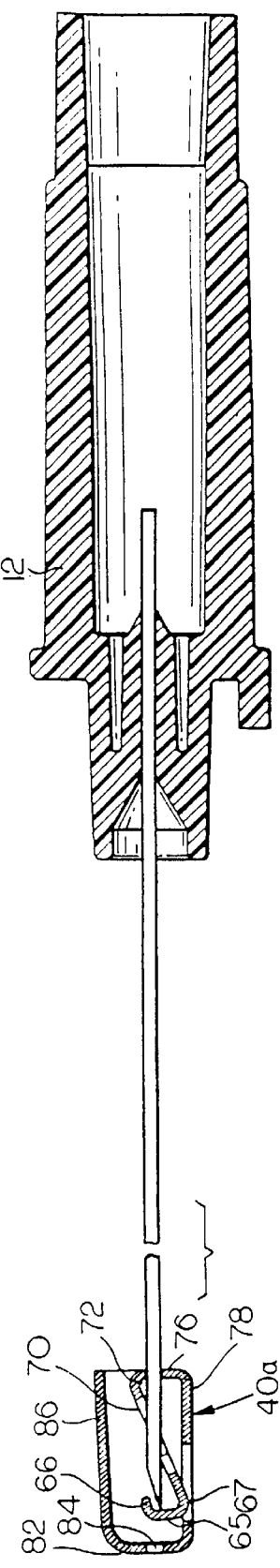

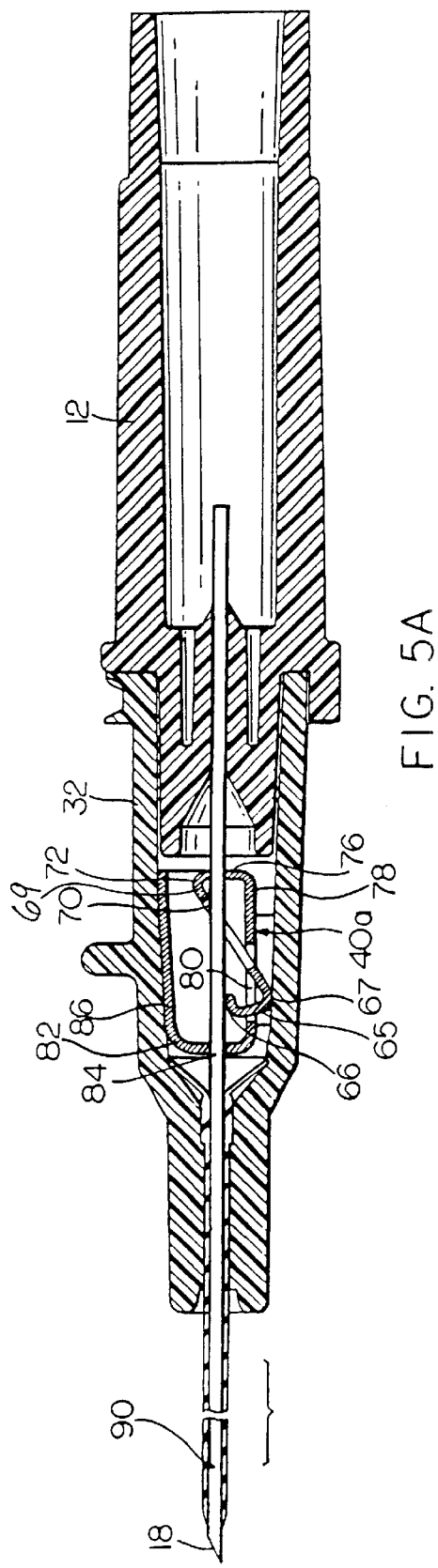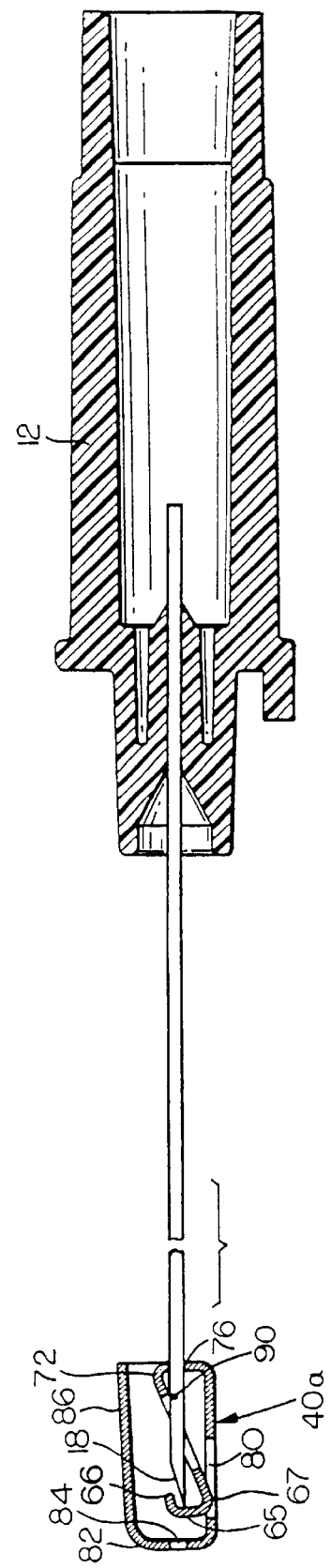
FIG. 5A
FIG. 5B

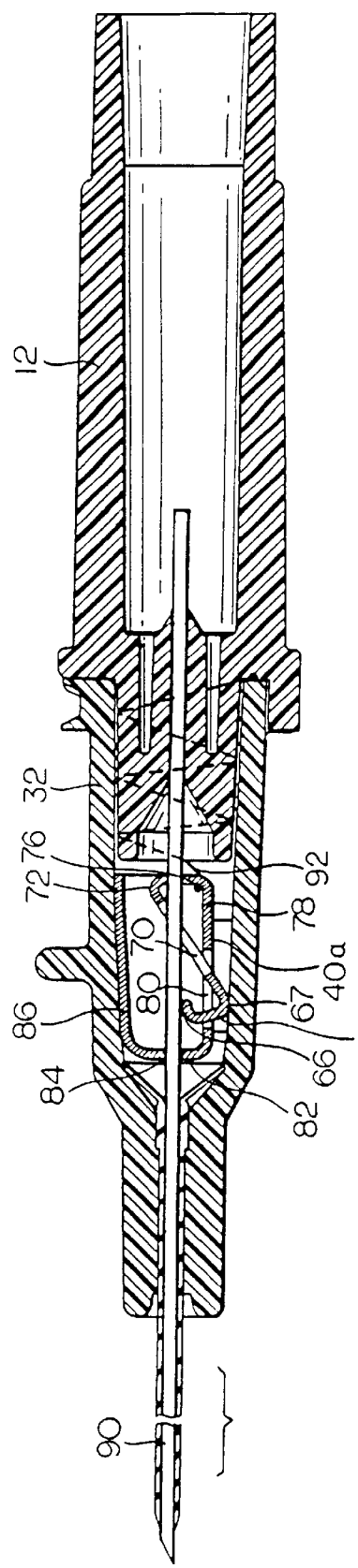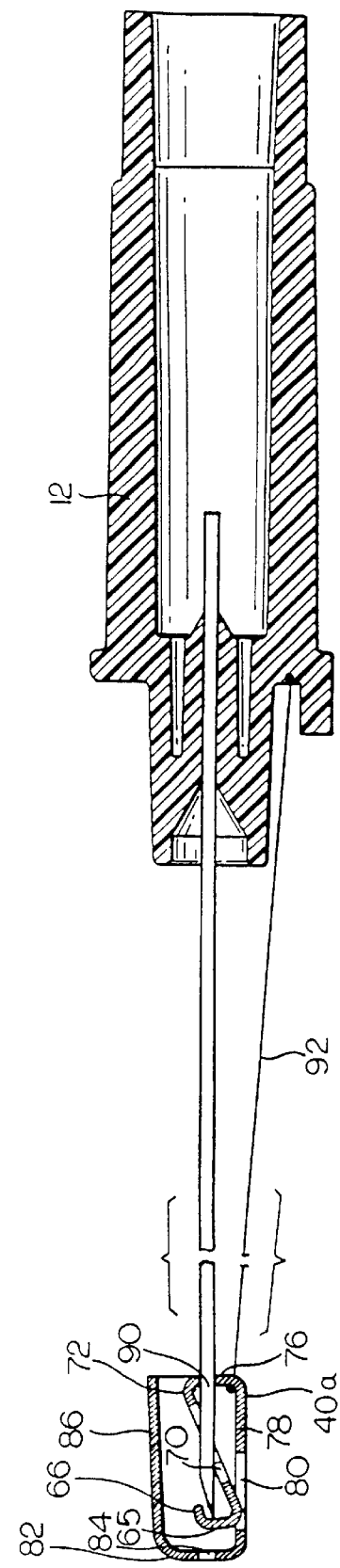
FIG. 6A
FIG. 6B

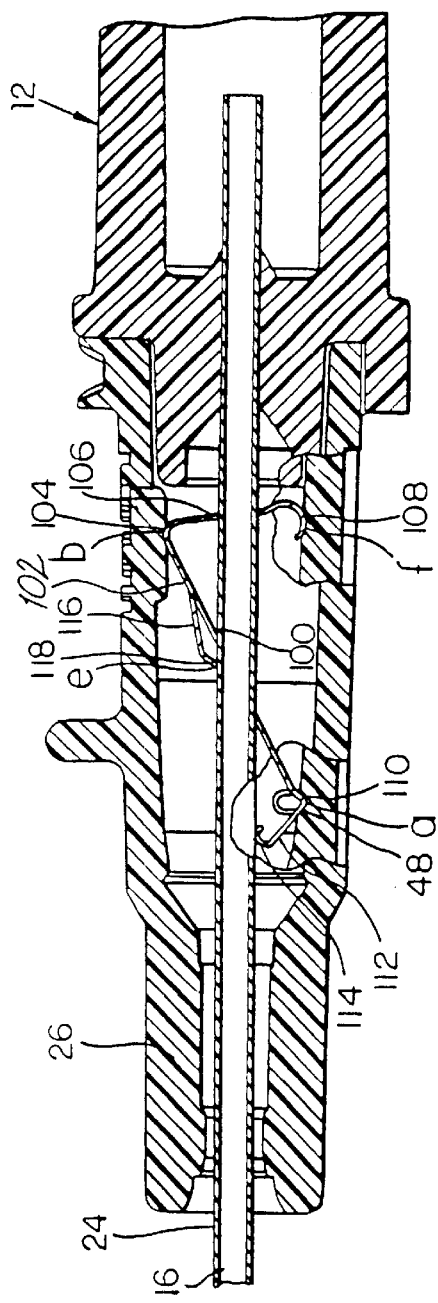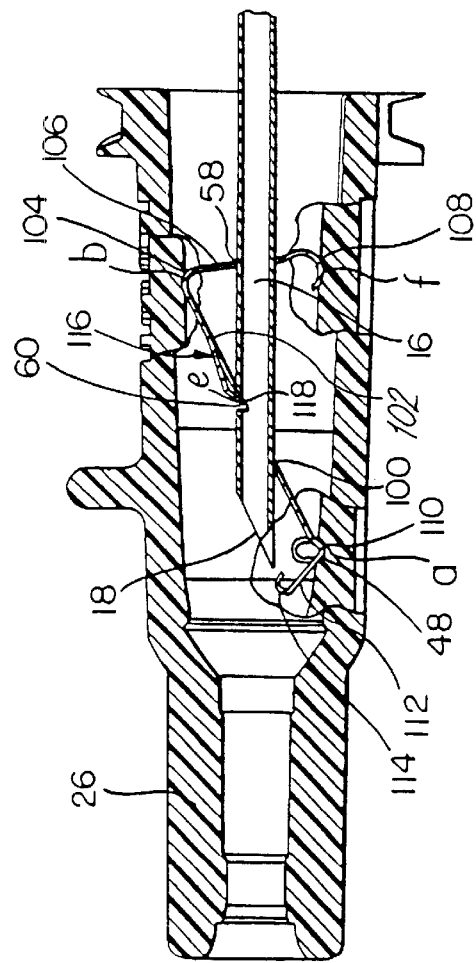
FIG. 7A
FIG. 7B

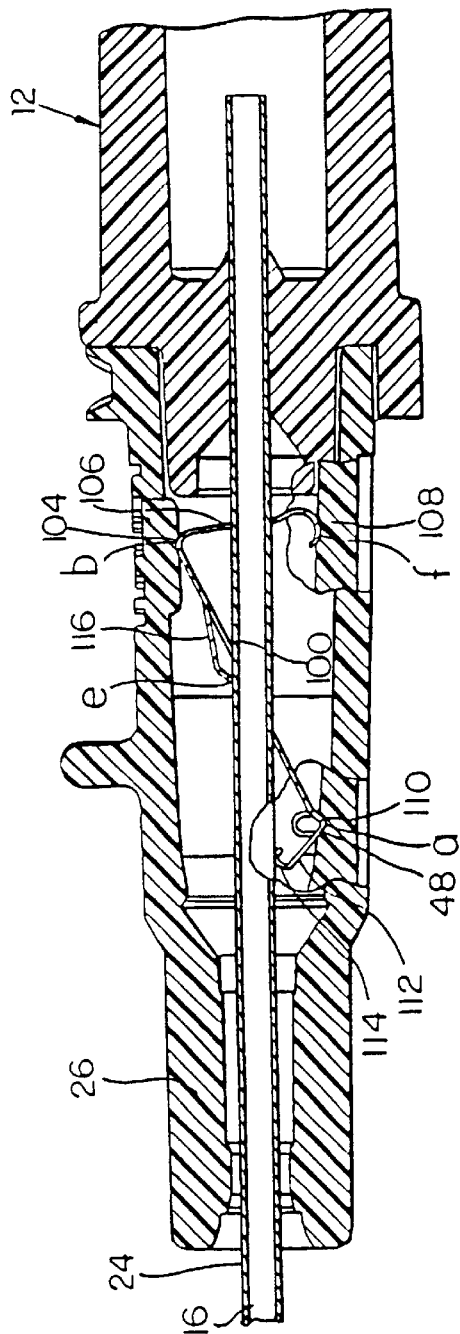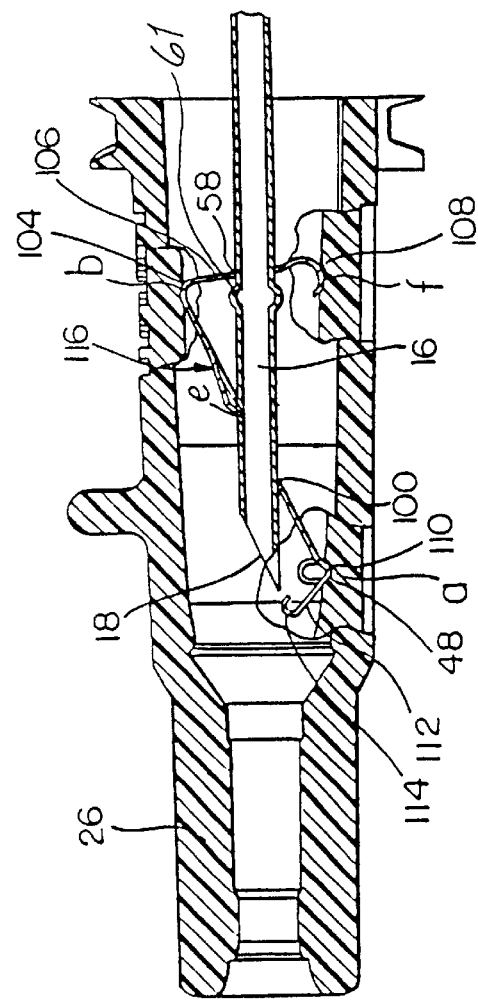
FIG. 7D
FIG. 7E

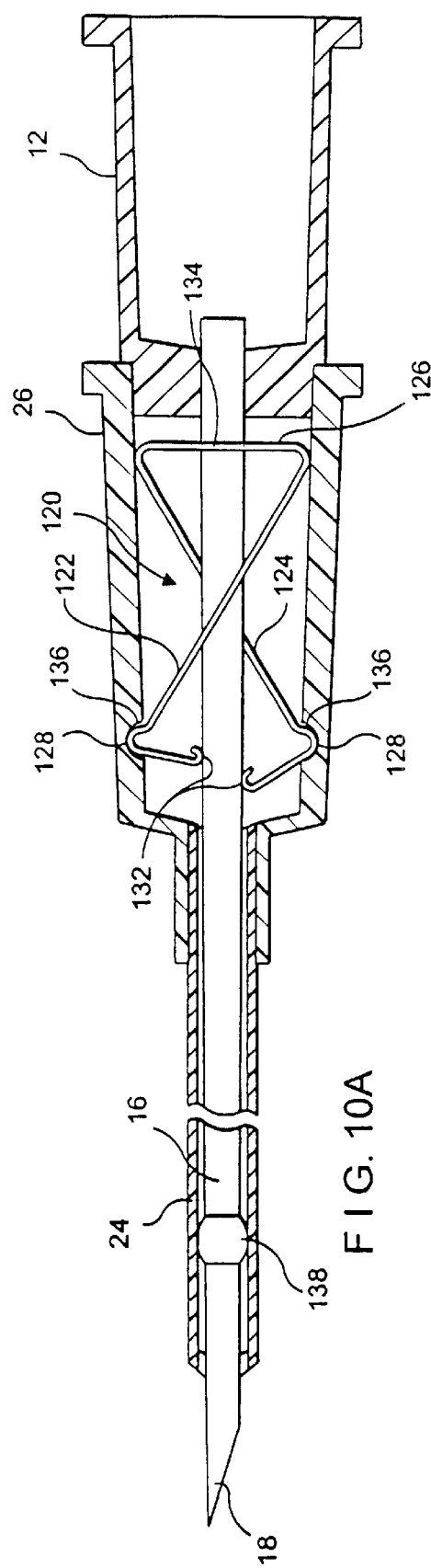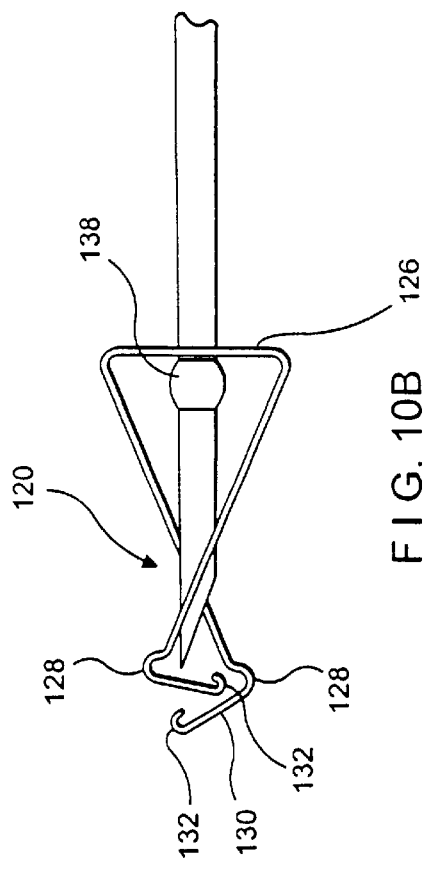
FIG. 10A
FIG. 10B

SPRING DIP SAFETY IV CATHETER

TECHNICAL FIELD

This is a continuation-in-part of application Ser. No. 09/097,170, filed Jun. 12, 1998, which is a continuation-in-part of application Ser. No. 08/915,148 filed on Aug. 20, 1997.

This invention relates generally to intravenous (IV) catheters, and, in particular, to a safety IV catheter in which the needle tip is automatically covered after needle withdrawal to prevent the health-care worker from making accidental contact with the needle tip.

BACKGROUND OF THE INVENTION

I.V. catheters are primarily used to administer fluids, sometimes containing medications, directly into a patient's vascular system. The catheter is inserted into a patient's vein by a health care worker by using a handheld placement device that includes a sharp tip needle. The needle is positioned in the interior hollow portion of the catheter with its tip extended slightly beyond the edge of the catheter. The end of the apparatus opposite the needle tip is made up of the needle connected to a needle hub which is capable of being held by the health care worker during the insertion procedure.

The insertion procedure contains four basic steps: (1) the health care worker inserts the needle and catheter together into the patient's vein; (2) after insertion into the vein with the needle point, the catheter is forwarded into the vein of the patient by the health care worker pushing the catheter with his or her finger; (3) the health care worker withdraws the needle by grasping the hub end (opposite the point end) while at the same time applying pressure to the patient's skin at the insertion site with his or her free hand; and (4) the health care worker then tapes the now inserted catheter to the patient's skin and connects the exposed end of the catheter, the catheter hub, to the source of the fluid to be administered into the patient's vein.

The problem is that immediately after the withdrawal of the needle from the patient's vein, the health care worker who is, at this time, involved in at least two urgent procedures must place the exposed needle tip at a nearby location and address the tasks required to accomplish the needle withdrawal. It is at this juncture that the exposed needle tip creates a danger of an accidental needle stick occurring, which under the circumstances, leaves the health care worker vulnerable to the transmission of various, dangerous blood-borne pathogens, including AIDS and hepatitis.

This danger to the health care worker from accidental needle sticks has caused an impetus for the development of a safer IV catheter in which the occurrence of such accidental needle sticks is prevented. Safety catheters that have been developed to achieve this result are disclosed, for example, in Lemieux Reissue Patent No. Re. 34,416, Crawford U.S. Pat. No. 5,558,651, McLees U.S. Pat. No. 5,135,504, Gaba U.S. Pat. No. 5,697,907, and Dombrowski U.S. Pat. No. 4,978,344. Kulli U.S. Pat. No. 4,929,241 and Chamuel U.S. Pat. No. 5,053,017 disclose a protective needle guard for use with a hypodermic needle.

The prior art safety catheters all exhibit one or more drawbacks that have thus far limited their usefulness and full acceptance by health-care workers. For example, in the safety catheter disclosed in the Lemieux patent, the force required to engage the needle slot within the guard flange is relatively great and would interfere with the removal of the needle. Reducing this force to a more acceptable level would create the possibility of the needle guard remaining in the catheter hub after the needle is removed from the catheter. As a result, the safety catheter disclosed in the Lemieux patent would not consistently function in a reliable manner.

Similarly, the user of the safety catheter disclosed in the Dombrowski patent would have to exert a considerable force to remove the protective cap from the catheter hub, when the cap engages a needle. The safety catheter disclosed in the Dombrowski patent would also be relatively expensive to fabricate because of its inclusion of a flexible flange and a tether.

The McLees protective device requires an irksome, extra pulling action or tug on the needle guard through a retention ring to remove the protected needle from the catheter hub. The McLees device also requires the assembly of two separate components and is thus relatively costly to manufacture. In addition, the needle in the McLees device includes a larger diameter portion near and at the needle tip. This feature of the McLees device would require that the remainder of the needle be of a lesser diameter which would have the adverse effect of slowing the blood flashback through the needle.

SUMMARY OF THE INVENTION

It is accordingly an object of the present invention to provide a safety IV catheter, which reliably and automatically prevents accidental, inadvertent contact with the needle tip after use.

It is a further object of the invention to provide a safety catheter which provides reliable protection to the health care practitioner against needle sticks without requiring any change in the manner of use of the safety catheter by the practitioner.

It is another object of the present invention to provide a safety IV catheter of the type described which is relatively simple and inexpensive to manufacture.

It is yet a further object of the present invention to provide a safety catheter of the type described in which removal of the needle from the needle guard after use is prevented.

To these ends, the safety IV catheter of the invention includes a resilient spring clip needle guard that includes a distal or front end and a proximal or rear wall. The spring clip is inserted into the catheter hub and is urged by the needle shaft into contact with the inner walls of the catheter hub so that the needle guard is reliably retained therein. When the needle is withdrawn from the catheter, the force it had previously exerted on the needle guard is released causing the needle guard to pivot within the catheter hub until it clamps onto the needle shaft. At this time, the distal end wall of the needle guard blocks the distal pointed end tip of the needle. In addition, the spring clip and protected needle onto which it is clamped can be readily and safely removed from the catheter hub. The needle may be provided with a slot or a bulge which cooperates with the needle guard to prevent the inadvertent removal of the needle from the needle guard after their removal from the catheter hub.

In another embodiment of the spring clip safety catheter of the invention, a retaining groove or bump is formed in the inner wall of the catheter hub, which, in the ready position, engages a lower arm of the spring clip to aid in the retention of the spring clip in the catheter hub.

In yet a further embodiment of the spring clip safety catheter of the invention, a slot is formed in the needle. After the spring clip has pivoted to its retracted position and the needle is clamped by the spring clip, further movement of the needle in the proximal direction will cause the rear or proximal arm of the spring clip to seat in the slot, thereby to more securely clamp the needle shaft to the spring clip.

In a further embodiment of the spring clip catheter guard of the invention, a tether is connected to the needle hub and the spring clip guard to prevent the spring clip guard from being pulled off the protected needle without requiring an excessive clamping force therebetween.

In yet a further embodiment of the invention the spring clip needle guard is in the form of resilient intersecting arms, each terminating at a distal guard wall. When the needle is in the ready position it passes through the guard and urges the resilient arms away from each other and against the inner wall of the catheter hub. When the needle is retracted past the guard walls, the resilient arms spring to the safety position in which both of the guard walls are positioned distally from the needle tip, thereby to form a barrier that prevents inadvertent contact with the needle tip.

To the accomplishment of the above and to such further objects as may hereinabove appear, the present invention relates to a safety IV catheter as described with respect to presently preferred embodiments in the following specification, as considered with the accompanying drawings, in which:

BRIEF DESCRIPTION OF THE DRAWINGS

FIGS. 1A and 1B are views in partial cross-section of a safety IV catheter in accordance with a first embodiment of the invention in the ready and retracted positions, respectively;

FIGS. 2A and 2B are views in partial cross-section of a safety IV catheter in accordance with a second embodiment of the invention in the ready and retracted positions, respectively;

FIGS. 3A and 3B are views in partial cross-section of a safety IV catheter in accordance with a third embodiment of the invention in the ready and retracted positions, respectively;

FIGS. 4A and 4B are views in partial cross-section of a safety IV catheter in accordance with a fourth embodiment of the invention in the ready and retracted positions, respectively;

FIGS. 5A and 5B are views in partial cross-section of a safety IV catheter in accordance with a fifth embodiment of the invention in the ready and retracted positions;

FIGS. 6A and 6B are views in partial cross-section of a safety IV catheter in accordance with a sixth embodiment of the invention in the ready and retracted positions, respectively;

FIGS. 7A, 7B and 7C are views in partial cross section of a safety IV catheter in accordance with a further embodiment of the invention in the ready, engaged and retracted or protected positions, respectively;

FIGS. 7D and 7E are views similar to FIGS. 7A and 7B of a possible variation to the embodiment of the invention illustrated therein;

FIGS. 10A and 10B are views in partial cross-section of a safety IV catheter in accordance with still a further embodiment of the invention shown in the ready and protected positions, respectively;

DESCRIPTION OF THE PREFERRED EMBODIMENTS

Figure 1C:
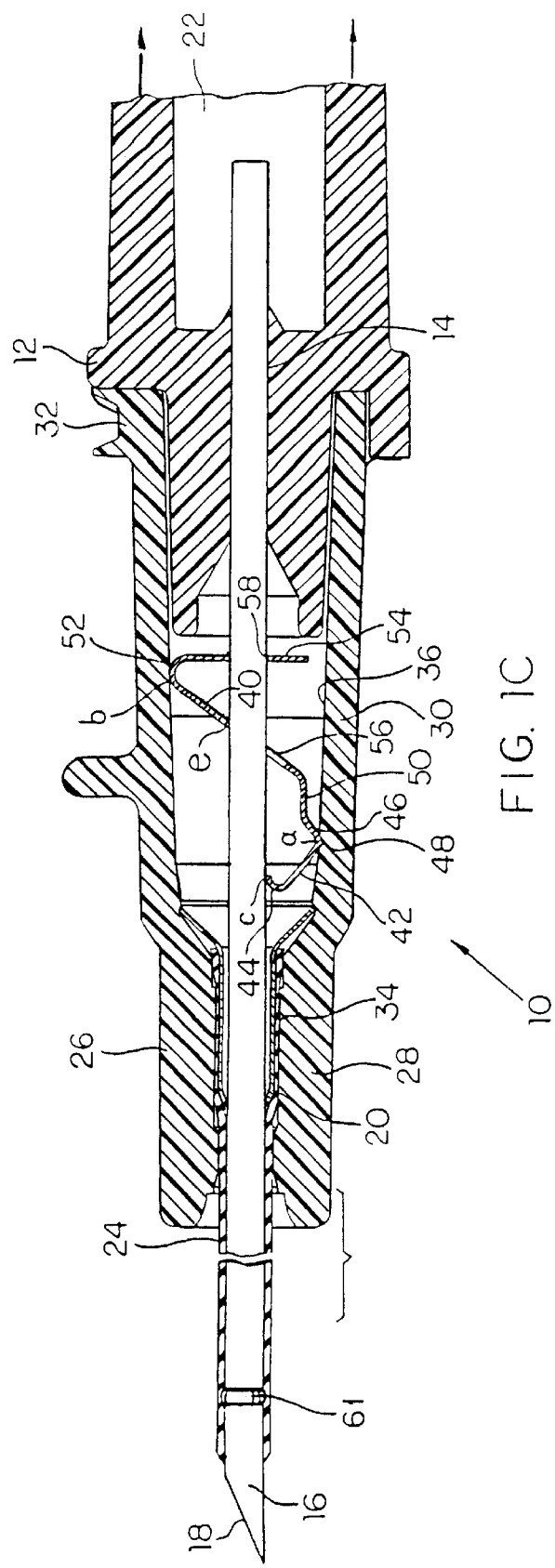
FIGS. 1C and 1D are views similar to FIGS. 1A and 1B of a possible variation to the embodiment illustrated therein.

The safety IV catheter of the invention, generally designated 10, in the embodiment illustrated in FIGS. A and 1B, includes a needle hub 12 that includes an axial opening 14 which securely receives the proximal end of a needle 16 having a sharpened tip 18. The needle hub 12, as is conventional, is hollow and includes a flash chamber 22. As is also conventional, the needle 16 is received within a hollow tubular catheter 24, the proximal end of which is concentrically affixed within the distal end of a catheter hub 26 having a distal section 28 and a contiguous, larger diameter proximal section 30.

The catheter hub 26 terminates at its proximal end in a luer fitting 32 adapted to receive a tubing set, which in a known manner, administers intravenous fluid into the patient. The catheter 24 is secured within an axial passageway 34 in distal hub section 28 by means of a sleeve 20 received within passageway 34, which engages the proximal end of the catheter. Passageway 34 communicates at its proximal end with a flash chamber 36 formed in hub section 30.

In the ready position of the catheter shown in FIG. 1A, the distal end of the needle hub 12 is snugly received in the proximal end of the interior of chamber 36 such that the needle 16 extends through the chamber 36, the passageway 34 and distally beyond the catheter hub 26 and catheter 24 so that its tip extends beyond the tapered distal end of the catheter.

In use, the distal tip of the needle and the catheter are inserted into a patient's vein. Thereafter, the health care practitioner manually places the catheter further into the vein and then withdraws the needle by grasping and moving by hand the proximal end of the needle hub 12. The luer of the catheter hub 26 is then fitted with a source of the fluid that is to be administered into the patient's vein.

In accordance with the present invention, as the needle 16 is being withdrawn from the patient, a protective needle guard 40 located within hub chamber 36 automatically snaps into a retracted position in which it blocks access to the distal needle tip and prevents further distal movement of the needle tip, thereby to prevent accidental contact by the health care practitioner with the needle tip.

As shown in FIGS. 1A and 1B, the needle guard 40 is in the form of a unitary spring clip that is preferably made of a resilient metal such as stainless steel. The spring clip includes a resilient portion which comprises a distal arm 42 terminating at its upper end in a curved lip 44, and at its lower end in a pointed end 46, which, in the embodiment of FIG. 1, is received within a mating groove 48 formed in the lower interior wall of catheter hub section 30.

The spring clip needle guard 40 further includes a transverse segment 50 that extends upward and proximally from lower pointed end 46 and terminates at a U-shaped upper end 52. In the ready position of the spring clip shown in FIG.

1A, upper end 52 abuts against the upper interior wall of the catheter hub section 30. The spring clip guard 40 further includes a vertical arm 54 that extends downward from the U-shaped upper end 52 and terminates above the lower wall of catheter hub section 30. Transverse segment 50 and proximal vertical arm 54 respectively include axially aligned openings 56, 58 through which the shaft of needle 16 is free to pass and axially move. The diameter of opening 58 is slightly greater than that of the needle shaft, whereas the diameter of the opening 56 is greater than that of opening 58.

In the ready position of the catheter prior to needle withdrawal, the shaft of needle 16 engages the curved lip 44 of the spring clip needle guard 40, thereby to exert an essentially downward force on the resilient spring clip. That force causes the lower end 46 of the spring clip to seat securely in groove 48 at point a. That contact, in addition to the abutment of the upper end 52 of the spring clip with the upper interior wall at the catheter hub at point b, securely maintains the spring clip needle guard 40 in the ready position within the catheter hub.

As the needle 16 is retracted to the left, as viewed in FIG. 1A, to its fully retracted position shown in FIG. 1B, after catheter insertion into the patient's vein, the distal tip of the needle moves proximally past the curved lip 44 of the spring clip needle guard 40 at point c, at which time the downward force previously exerted by the needle shaft on the spring clip is released.

As a result of the needle 16 moving proximally past point c, the retention force on spring clip needle guard 40 in the catheter hub is released causing the spring clip needle guard 40 to pivot or snap in a clockwise direction to the retracted position shown in FIG. 1B. As therein shown, distal arm 42 of the needle guard 40 blocks the distal path of the needle 16. Simultaneously with the blocking and releasing actions, the spring clip guard 40 becomes securely clamped onto the needle shaft at points d and e, thereby to securely lock the needle guard 40 onto the needle shaft. At this time, the needle 16 and needle guard 40 can be removed together from the catheter hub 26, and the tip of the needle cannot be pushed past the needle guard because it is blocked by the distal arm 42 and lip 44 of the needle guard.

If desired, a slot 60 may be formed in the needle shaft slightly proximal to the needle tip. When the needle and needle guard are in their retracted and clamped positions (FIG. 1B), slot 60 is positioned slightly distal to the clamping point e of the transverse segment of the needle guard 40 such that if a subsequent attempt is made to move the needle further in a rearward or proximal direction, the transverse segment 50 at point e will seat into slot 60, thereby to provide an additional force to retain the needle guard 40 on the needle 16 in the protected position in which access to the needle tip is prevented.

Figure 1D:
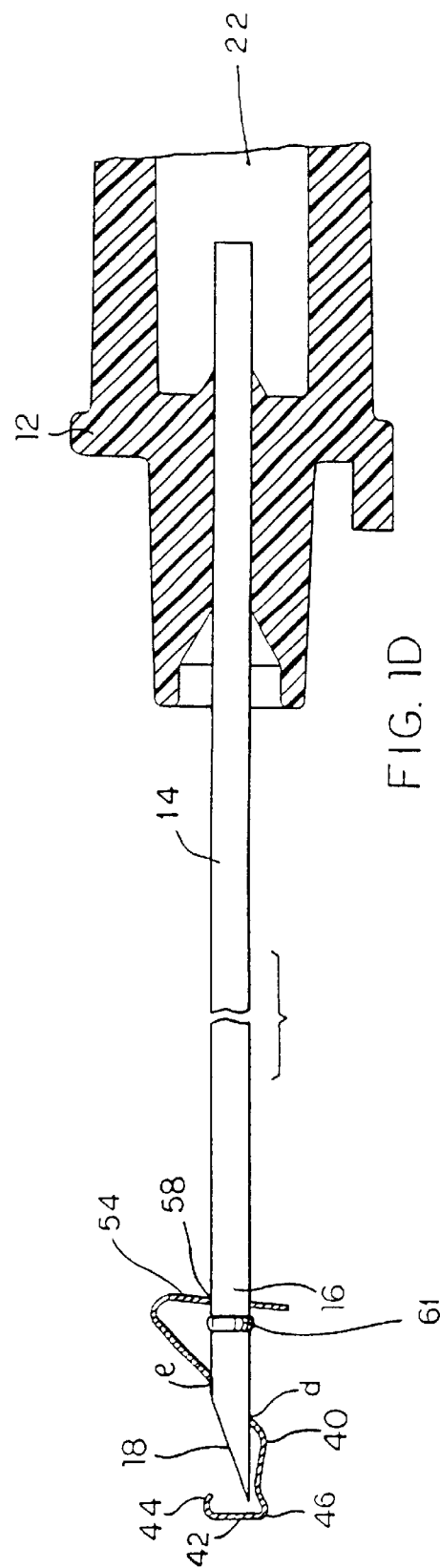

The safety IV catheter illustrated in FIGS. 1C and 1D is the same as that illustrated in FIGS. 1A and 1B, except that the slot 60 in the needle shaft in the latter is replaced in the former by a bulge 61 whose diameter is greater than that of opening 58 in vertical arm 54. If an attempt is made to move the protected needle illustrated in FIG. 1C in the rearward or proximal direction, bulge 61 will engage wall 54 and will thus not be able to pass through opening 58, so as to prevent further proximal movement of the needle and removal of the needle from the needle guard, as defined.

The embodiment of the invention illustrated in FIG. 2 is similar to that of FIG. 1 except that instead of the groove formed in the lower wall of the catheter hub that engages the lower end of the spring clip, a retaining bump 62 is formed in that wall against which the lower end 46 of the needle guard 42 seats when the needle guard 40 is in the ready position in FIG. 2A.

The embodiment of the invention illustrated in FIGS. 3A and 3B is essentially the same as that of FIG. 2 with the addition of a tether 64 secured at one end to the needle hub 12 and at its other end to proximal arm 54 of the spring clip needle guard 40. As shown in FIG. 3B, the tether 64 is extended to its full length when the needle hub is retracted to achieve needle removal so as to more securely retain the needle hub 12 and the spring clip needle guard 40 when the latter is clamped onto the needle when in the retracted position, in which, as described above, the distal arm 42 of the spring clip prevents access to the needle tip, and the needle guard 40 and needle are released from the catheter hub.

FIGS. 4A and 4B illustrate a spring clip needle guard embodying the principles of the invention in an alternative configuration. As therein shown, the spring clip needle guard 40a includes a resilient portion comprising a distal arm 65 terminating at its upper end in a curved lip 66, and at its lower end in a U-shaped portion 67 which, in the ready position illustrated in FIG. 4A, contacts a bump 68 formed in the lower inner wall of the catheter hub.

A resilient transverse segment 69 having a central opening 70 extends proximally and upwardly and terminates at an upper U-shaped portion 72. A proximal end wall 74 having an opening 76 depends vertically from portion 72 and then extends distally in a horizontal lower segment 78, which has an opening 80 through which the lower halves of distal arm 65 and transverse segment 69 extend in the ready position of the needle guard. Segment 78 at its distal end extends upwardly at a front wall 82, which has a central opening 84 axially aligned with openings 70, 76. At its upper end, distal front wall 82 extends in the proximal direction in an upper segment 86 which, as shown in FIG. 4A, contacts the upper inner wall of the catheter hub along substantially its entire length.

As shown in FIG. 4A, when the catheter is in the ready position, the needle shaft passes through openings 70, 76 and 84 and rests on curved lip 66, urging arm 65 against bump 68 in the lower wall of the catheter hub. That engagement along with the resilient engagement of upper segment 86 with the upper interior wall of the catheter hub retains the spring clip 40a in its ready position within the catheter hub.

When the needle hub and needle are retracted to the right, as viewed in FIG. 4A, by a sufficient amount, the needle tip passes below lip 66 and then releases its downward force on arm 65. As described above, with reference to the first-described embodiment, this release of engagement of the needle shaft and spring clip arm 65 causes arm 65 to snap upwards to the retracted position illustrated in FIG. 4B, in which arm 65 and lip 66 extend over the needle tip and thereby prevent accidental contact with the needle tip as desired. In this condition, the needle guard is clamped onto the needle shaft in essentially the same manner described above with respect to the first-described embodiment, and the needle and needle guard clamped thereto can be readily removed from the catheter hub, also as described above, and as shown in FIG. 4B.

The embodiment of the needle guard illustrated in FIGS. 5A and 5B is essentially the same as that shown in FIGS. 4A and 4B with the addition of a slot 90 near the distal tip end of the needle. When the needle and needle guard are in their retracted and clamped position (FIG. 5B), slot 90 is positioned slightly distal to the clamping point of the transverse segment 69 such that if a subsequent attempt is made to move the needle further in a rearward or proximal direction, the transverse segment 69 will seat into slot 90, thereby to provide an additional force to retain the needle guard in the needle in the protected position in which access to the needle tip is prevented.

The embodiment of the invention illustrated in FIGS. 6A and 6B is the same as that illustrated in FIGS. 4A and 4B except for the inclusion of a tether 92 secured at one end to the needle hub and at its other end to the proximal wall of the spring clip needle guard. As shown in FIG. 6A, in the ready position, the tether is wound around the distal end of the needle hub. As shown in FIG. 6B, when the needle and needle guard are in their retracted position, the tether is extended to its full length and adds in the retention of the needle guard to the needle hub. If desired, the embodiment of the invention embodiment illustrated in FIGS. 6A and 6B could also include a needle slot as in the embodiment of the invention illustrated in FIGS. 5A and 5B.

Figure 7C:
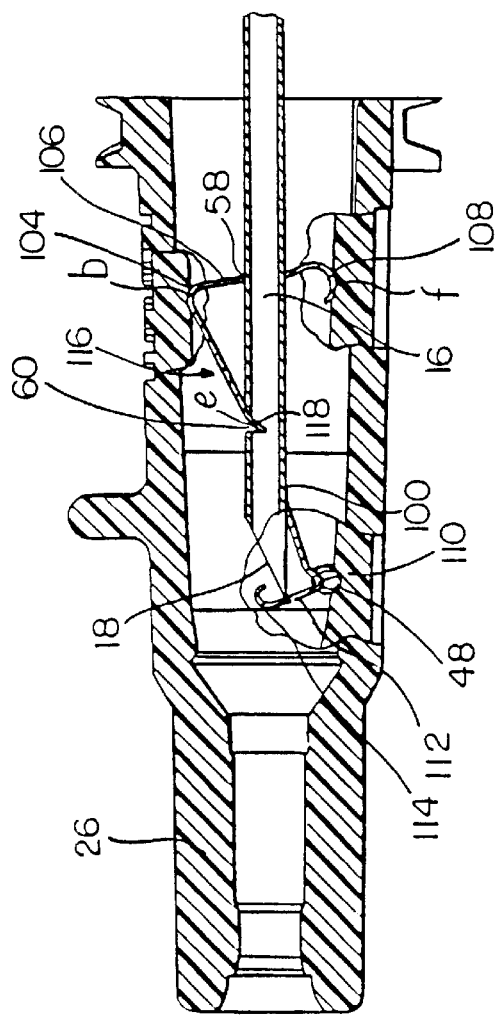
Figure 9:
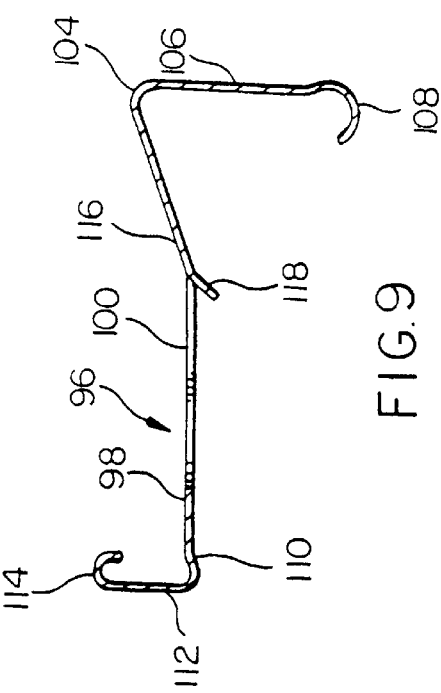
FIG. 9 is a cross-section of the spring clip needle guard of FIG. 8.
Figure 8:
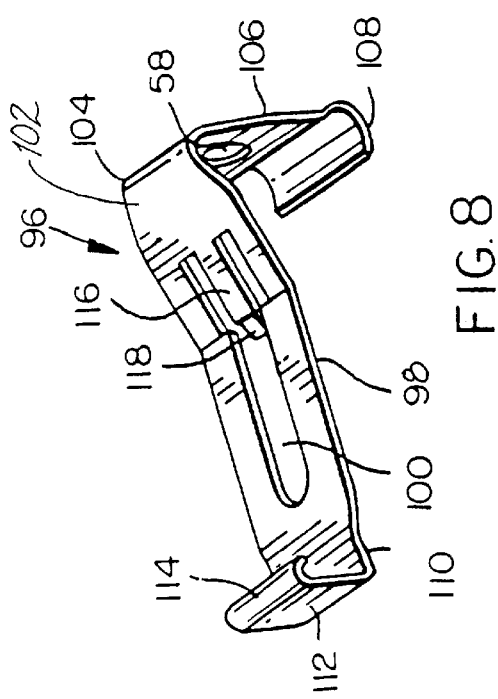
FIG. 8 is a perspective of the spring clip needle guard used in the embodiment of FIG. 7.

The embodiment of FIGS. 7A–C, differs from the previously described embodiments primarily with regard to the construction and operation of the spring clip needle guard 96. As shown in FIGS. 8 and 9, the spring clip 96 comprises a resilient portion which includes a central transverse section 98 which includes a central slot 100. A sloping section 102 extends from section 98 in the proximal direction and terminates at a curved end 104 from which a proximal vertical arm 106 extends. Arm 106 terminates at its lower end in a U-shaped section 108. The distal end of transverse section 98 terminates in a curved section 110 from which a vertical proximal arm 112 extends. Distal arm 112 terminates at its upper end in a curved arm 114.

A cutout portion in section 98 defines a flexible flap 116 which terminates at its distal free end in a downwardly sloping locking tab 118. As in the prior embodiments, proximal arm 106 includes an opening 58.

As shown in FIG. 7A, spring clip needle guard 96, when in the ready position illustrated therein, is inserted within catheter hub 26 so as to allow the needle 16 to pass through opening 58 and slot 100. As in the previously described embodiments, the curved end 104 abuts against the inner upper wall of the catheter hub 26 at point b, and curved section 110 seats within the mating groove 48 at point a formed in the lower, inner wall of the catheter hub. In addition, the lower curved section 108 contacts at a point f the lower, inner wall of the catheter hub 26 at a location proximal to point b.

In operation, the needle is initially withdrawn into the catheter hub until it reaches the tab engaged position illustrated in FIGS. 7B, in which as therein shown, the locking tab 118 is received within the needle groove or slot 60. At this point, the spring clip remains in contact with the inner wall of the catheter hub at points a, b and f, while the needle tip 18 engages curved end 114, thereby to urge section 110 into groove 48 at point c. The relative position of point f with respect to point b prevents the needle and clip from being prematurely released from the catheter hub by preventing the distal end of the clip from tipping upwards and the proximal end from slipping downward with the clip in the tab engaged position shown in FIG. 7B.

As the needle is withdrawn further away from the patient, as shown in FIG. 7C, the needle tip passes beyond curved end 114, thereby releasing the downward force that had been previously exerted on curved end 114 by the needle.

This sudden release of the downward force on the spring clip end causes the distal end of the spring clip 96 to pivot upward so that distal end 112 of spring clip 96 moves rapidly to a position in which it prevents or blocks motion of the needle in the distal direction. The spring clip 96 is retained on the needle 16 and will be removed from the catheter hub 26 when the needle is completely removed. Movement of the spring clip 96 from its protecting or retracted position shown in FIG. 7C is further prevented by the insertion of the locking tab 118 into the needle groove 60, which prevents the spring clip from rotating around the periphery of the needle. This, in turn, secures the spring clip on the needle even if the clip were subjected to a twisting and pulling force.

The safety IV catheter illustrated in FIGS. 7D and 7E is the same as that illustrated in FIGS. 7A and 7B, except that the slot 60 in the needle shaft in the latter is replaced in the former by a bulge 61 whose diameter is greater than that of opening 58 in vertical arm 54. If an attempt is made to move the protected needle illustrated in FIG. 7D in the rearward or proximal direction, bulge 61 will engage wall 54 and will not be able to pass through opening 58, so as to prevent any further proximal movement of the needle and removal of the needle from the needle guard, as desired.

Figure 11:
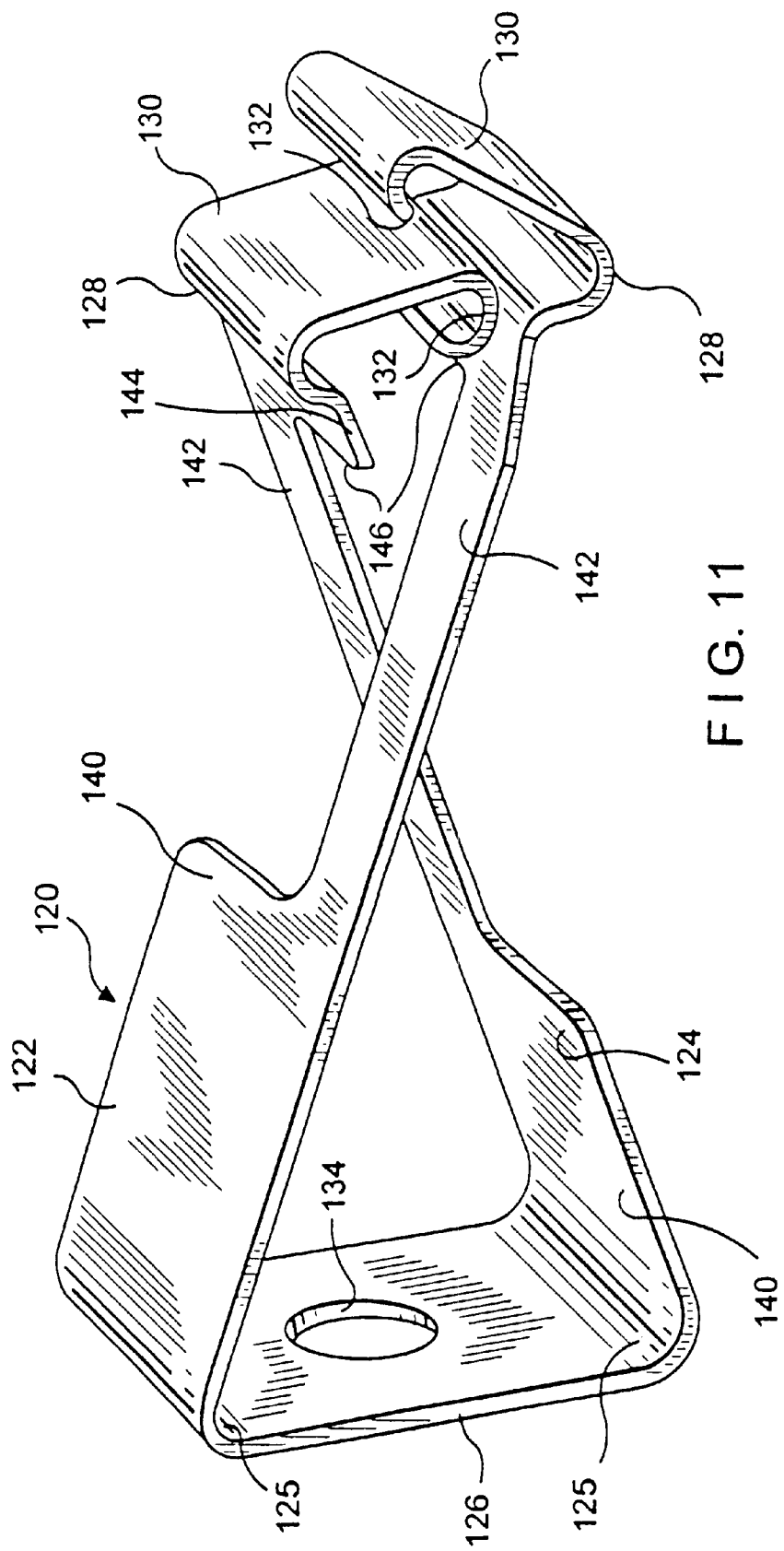
FIG. 11 is a perspective of the needle guard clip of the embodiment of FIG. 10.

The embodiment of the spring clip needle guard 120 disclosed in FIGS. 10A, 10B, and 11 comprises a resilient portion which comprises first and second arms 122 and 124 respectively joined at their proximal ends in a hinged arrangement at 125 to the ends of a rear wall 126. The distal ends of arms 122, 124 each include a curved protrusion 128 extending to a distal end wall 130, which in turn terminates in a lip 132. As seen best in FIG. 11, rear wall 126 includes a central opening 134, and arms 122 and 124 each include a narrow portion 142 that extends between a distal wide portion 140 and a proximal wide portion 144. A lateral clamping edge 146 is defined at the distal wide portion 144.

As shown in FIG. 10A, when the needle guard 120 is in its ready position, the curved protrusions 128 in each of arms 122, 124 are received in an annular groove or ring 136 formed in the inner wall of catheter hub 26, which, as in the prior embodiments, is removably fit into the distal end of a needle hub 12. Also as in the prior embodiment, a needle 16 having a sharpened tip 18 at its distal end is received within a tubular catheter 24, which is secured to the distal end of catheter hub 26. The proximal end of needle 16 passes through opening 134 in rear wall 126. Needle 16 includes an increased diameter bulge 138, which is sufficiently small to allow needle 16 to move axially along catheter 24, but greater in diameter than opening 134 for reasons to be described below.

In the ready position illustrated in FIG. 10A, the needle shaft passes through the needle guard and applies an outward radial force on resilient arms 122, 124 by means of its engagement with lips 132, so as to urge the curved protrusions 128 of each of the arms into the annular groove 136, so as to retain needle guard 120 in a fixed position within the inner wall of catheter hub 26. The shaft of needle 16 that passes through the needle guard 120 frictionally engages the inner edges of the narrow portions 142 of arms 122, 124 so as to further retain the needle in its ready position.

When the needle is retracted axially, to the right as viewed in FIG. 10A, within the catheter hub, and moves past the end lip 132 of the needle guard, the radial force previously exerted on arms 122, 124 of needle guard 120 is suddenly released. This causes the distal end walls 130 of the needle guard to be released from their seat in the annular groove 136 and to pivot inwards into the catheter hub until, as seen in FIG. 10B, the end walls 130 overlap one another at a location distally in front of the needle tip, thereby to form a barrier that prevents inadvertent contact with, and distal movement of, the needle tip. At the same time, the clamping edges 146 of the needle guard are urged against the needle tip to restrict further axial movement of the needle.

As also shown in FIG. 10B, the needle guard 120 and the needle clamped to the needle guard after needle retraction can be removed from the catheter hub as a unitary assembly, and safely discarded. If an attempt is made, intentionally or inadvertently, to pull the needle further to the right, as viewed in FIG. 10, out of the needle guard, the bulge 138 on the needle shaft will come into contact with the end wall 126, and since its diameter is greater than that of opening 134, the end wall 126 will at this point prevent any further axial movement of the needle out of the needle guard.

Figure 13A:
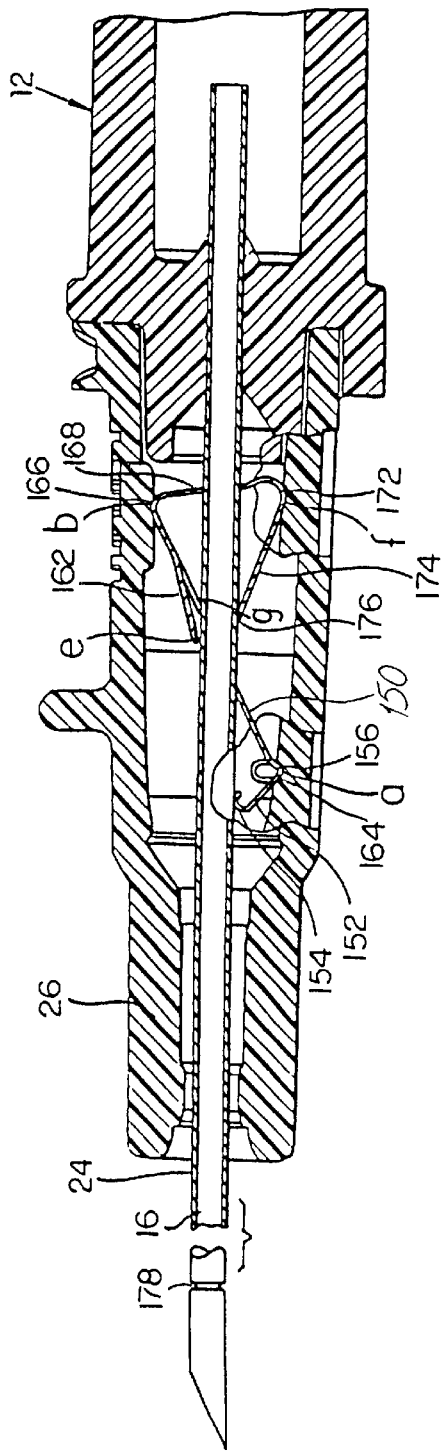
FIGS. 13A and 13B are cross-sectional views of the embodiment of the invention of FIG. 12 in the ready and protected positions, respectively.
Figure 13B:
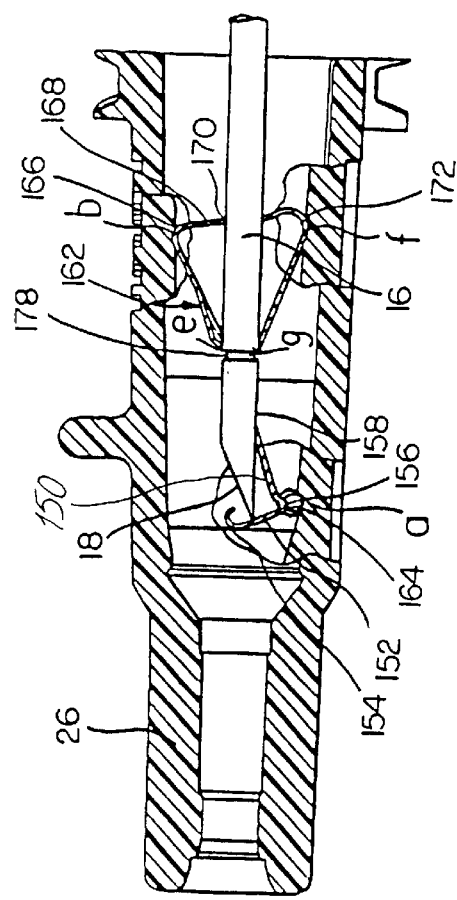
Figure 12:
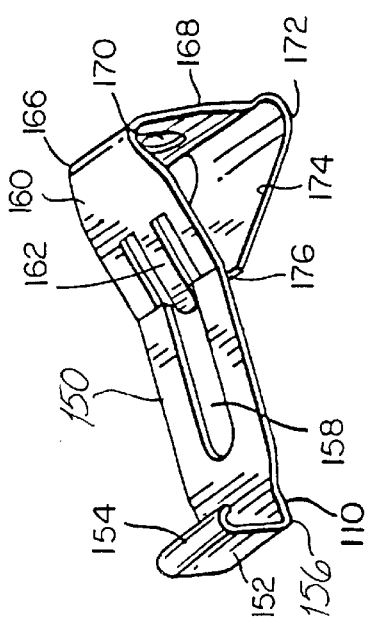
FIG. 12 is a perspective view of a safety IV catheter in accordance with another embodiment of the invention.

The spring clip guard of the invention, in the embodiment. illustrated in FIGS. 12, 13A and 13B, includes a resilient portion which comprises a transverse arm 150 terminating at its distal end at a distal end wall 152, which includes at its upper end a curved lip 154, and at its lower end a curved end 156. An elongated rectangular opening or slot 158 is provided in transverse arm 150. The proximal ends of transfer arm 150 and opening 158 terminate at an extension 160 extending upwardly at an angle from arm 150 and having a finger or flap 162 that extends toward opening 158.

The proximal end of extension 160 terminates at a curved end 166 from which a proximal end wall 168 extends downwardly. Wall 168, which includes an opening 170, terminates at its lower end at a curved section 172, from which extends an upwardly sloping arm 174 that terminates at a clamping edge 176. As can be seen in FIGS. 13A and 13B, a 360° circular groove 178 is formed about the circumferential wall of needle 16 slightly inwardly from the tip 18 of the needle.

In the ready position of the spring clip guard of FIG. 12, as illustrated in FIG. 13A, the shaft of the needle passes through aligned opening 170 in the rear wall 168 and opening 158 in the resilient transverse arm 150, and extends distally beyond the catheter hub. As in the prior embodiments described hereinabove, the needle shaft in this position exerts a downward radial force on arm 150 by means of its engagement with curved lip 154. This downward force urges the curved end 156 of the spring clip to seat firmly within a groove 164 formed in the inner wall of the catheter hub at point a.

At the same time, the upper curved end 166 of end wall 168 engages the inner wall of the catheter hub at point b, and the lower-curved end 172 of wall 168 engages the inner wall of the catheter hub at point f. Further engagement between the needle shaft and the spring clip is provided by the contact of finger 162 with the upper end of the needle shaft at point e, and between the clamping edge 176 and the lower surface of the needle shaft at point g. In this manner, the needle is securely but movably retained within the catheter hub in its ready position.

When the needle is retracted axially, to the right as viewed in FIGS. 13A and 13B, it eventually moves past its engagement with lip 154, thereby to suddenly release the radial force it had previously exerted on the resilient arm 150 of the needle guard. This release of engagement between the needle shaft and lip 154 allows the distal curved end 156 of the distal end wall 152 of the spring clip to be released from its seat in annular groove 164, so that arm 150 and end wall 152 pivot quickly into the interior of the catheter hub, as seen in FIG. 13B, to a position at which wall 152 forms a barrier to the needle tip. This positioning of wall 152 prevents inadvertent contact with the needle tip. The engagement of finger 162 and clamping edge 176 to opposing sides of the needle prevents further axial movement of the needle in either direction.

If an attempt is thereafter made to pull the needle axially further to the right, as viewed in FIG. 13B, the finger 162 will enter the circular groove 178 formed in the needle surface, thereby to prevent further axial movement of the needle in the proximal direction out of the needle guard.

It will thus be appreciated that the spring clip needle guard of the invention as employed in an IV catheter provides automatic and reliable protection of the needle tip upon needle retraction to prevent accidental contact with the needle tip by a health care practitioner. It will also be appreciated that modifications may be made to the embodiments of the invention specifically described hereinabove without necessarily departing from the spirit and scope of the invention.

What is claimed is:

1. An IV catheter apparatus comprising a tubular catheter having a proximal end and a distal end, a needle having a needle shaft and a tip, said needle being received within said tubular catheter when in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, a unitary needle guard positioned in the interior of said catheter hub and including a resilient portion engaged by said needle shaft when said needle is in its said ready position, a section of said resilient portion of said needle guard being urged by said needle shaft into contact with an interior wall of said catheter hub when said needle is in its said ready position, means formed on said interior wall of said catheter hub for engaging a segment of said needle guard for retaining said needle guard to said catheter hub during the movement of said needle between its said ready position and its said retracted position, said needle guard including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that contact between said section of said needle guard and said catheter hub is released, and a proximal end wall having a wall extending distally and upwardly from its lower end and terminating at a clamping edge for engaging said needle shaft when said needle is in its said ready position, said needle guard further including means for clamping said needle guard to said needle upon the movement of said needle guard to its said blocking position.

2. The catheter apparatus of claim 1, in which said distal wall of said needle guard is contiguous with said resilient portion, said distal wall terminating at a curved lip engaging the underside of said needle shaft when said needle is in its said ready position.

3. The catheter of claim 2, in which said needle guard further includes a proximal arm and a transverse segment extending between said distal wall and said proximal arm, said clamping means including first and second engagement points on said proximal arm and said transverse segment respectively, which are urged against opposing locations on said needle shaft when the needle is in the retracted position, thereby to clamp said needle guard to the needle shaft.

4. The catheter of claim 3, further including a bump formed in said inner wall of said catheter hub, said bump engaging said needle guard in said ready position to aid in retaining said needle guard in said ready position.

5. The catheter of claim 4, in which a slot is formed in said needle shaft at a location proximal to said needle tip, said slot being positioned slightly distal of said contact point of said needle guard proximal arm so that upon additional proximal axial movement of said needle said contact point on said proximal arm of said needle guard is received in said needle slot.

6. The catheter of claim 5, further comprising a needle hub affixed to said proximal end of the needle and further comprising a tether attached at one end to said needle hub and at its other end to said needle guard.

7. The catheter of claim 3, further including a groove formed in said inner wall of said catheter hub, said groove engaging said needle guard in said ready position to aid in retaining said needle guard in said ready position.

8. The catheter of claim 7, in which said needle guard further includes an upper end wall contiguous with said transverse segment and proximal to said resilient portion and in contact with an opposed interior wall of the catheter hub in the ready position.

9. The catheter of claim 8, in which said needle guard includes a proximal end wall extending from said resilient portion and including an opening allowing said needle to pass therethrough, said needle further including a large diameter segment on the needle shaft inward of said needle tip, the diameter of said large diameter segment being greater than that of said opening in said proximal wall.

10. The catheter of claim 7, in which a slot is formed in said needle shaft at a location proximal to said needle tip, said slot being positioned slightly distal of said contact point of said needle guard proximal arm so that upon additional proximal axial movement of said needle said contact point on said proximal arm of said needle guard is received in said needle slot.

11. The catheter of claim 10, further comprising a needle hub affixed to said proximal end of said needle and further comprising a tether attached at one end to said needle hub and at its other end to said needle guard.

12. The catheter of claim 10, in which said needle guard further includes an upper end proximal to said resilient portion and in contact with an opposed interior wall of the catheter hub when said needle is in said ready position.

13. The catheter of claim 3, in which said needle guard further includes an upper end contiguous with said transverse segment and proximal to said resilient portion and in contact with an opposed interior wall of the catheter hub when said needle is in the ready position.

14. The catheter of claim 2, further including a groove formed in said inner wall of said catheter hub, said groove engaging said needle guard in said ready position to aid in retaining said needle guard in said ready position.

15. The catheter of claim 14, in which said needle guard further includes an upper end proximal to said resilient portion and in contact with an opposed interior wall of the catheter hub when said needle is in said ready position.

16. The catheter of claim 2, further comprising a bump formed in said inner wall of said catheter hub, said bump engaging said needle guard in said ready position to aid in retaining said needle guard in said ready position.

17. The catheter of claim 2, in which said needle guard further includes an upper end proximal to said resilient portion and in contact with an opposed interior wall of the catheter hub when said needle is in its said ready position.

18. The catheter of claim 1, in which said needle guard further includes a proximal arm and a transverse segment extending between said distal wall and said proximal arm, said clamping means including first and second engagement points on said proximal arm and said transverse segment respectively, which are urged against opposing locations on said needle shaft when said needle is in the retracted position, thereby to clamp said needle guard to said needle shaft.

19. The catheter of claim 18, further including a groove formed in said inner wall of said catheter hub, said groove engaging said needle guard in said ready position to aid in retaining said needle guard in said ready position.

20. The catheter of claim 19, in which said needle guard further includes an upper end wall contiguous with said transverse segment and proximal to said resilient portion and in contact with an opposed interior wall of the catheter hub in the ready position.

21. The catheter of claim 18, in which a slot is formed in said needle shaft at a location proximal to said needle tip, said slot being positioned slightly distal of said contact point of said needle guard proximal arm so that upon additional proximal axial movement of said needle said contact point on said proximal arm of said needle guard is received in said needle slot.

22. The catheter of claim 18, further comprising a bump formed in said inner wall of said catheter hub, said bump engaging said needle guard in said ready position to aid in retaining said needle guard in said ready position.

23. The catheter of claim 18, in which said needle guard further includes an upper end wall contiguous with said transverse segment and proximal to said resilient portion and in contact with an opposed interior wall of the catheter hub in the ready position.

24. The catheter of claim 1, in which a slot is formed in said needle shaft at a location proximal to said needle tip, said slot being positioned slightly distal of said contact point of said needle guard proximal arm so that upon additional proximal axial movement of the needle said contact point on said proximal arm of said needle guard is received in said needle slot.

25. The catheter of claim 24, further comprising a needle hub affixed to said proximal end of the needle and further comprising a tether attached at one end to said needle hub and at its other end to said needle guard.

26. The catheter of claim 24, in which said needle guard further includes an upper end proximal to said resilient portion and in contact with an opposed interior wall of the catheter hub when said needle is in said ready position.

27. The catheter of claim 1, further including a groove formed in said inner wall of said catheter hub, said groove engaging said needle guard when said needle is in its said ready position to aid in retaining said needle guard in said retaining contact with said inner wall of said catheter hub while said needle moves from its said ready position to its said retracted position.

28. The catheter of claim 27, in which a slot is formed in said needle shaft at a location proximal to the needle tip, said slot being positioned slightly distal of said contact point of said needle guard proximal arm so that upon additional proximal axial movement of said needle said contact point on said proximal arm of said needle guard is received in said needle slot.

29. The catheter of claim 28, further comprising a needle hub affixed to said proximal end of the needle and further comprising a tether attached at one end to the needle hub and at its other end to said needle guard.

30. The catheter of claim 27, in which said needle guard further includes an upper end proximal to said resilient portion and in contact with an opposed interior wall of the catheter hub when said needle is in said ready position.

31. The catheter of claim 1, further comprising a bump formed in said inner wall of said catheter hub, said bump engaging said needle guard in said ready position to aid in retaining said needle guard in said ready position.

32. The catheter of claim 1, in which said needle guard further includes an upper end proximal to said resilient portion and in contact with an opposed interior wall of the catheter hub in said ready position.

33. The catheter of claim 1, in which said needle guard further comprises a proximal arm having a lower curved segment in contact with an inner wall of said catheter hub when said needle is in its said ready position.

34. The catheter of claim 33, in which said proximal arm further includes an upper end in engagement with an opposed location of said inner wall of said catheter hub distal to the point of contact with said lower curved segment when said needle guard is in its said ready position.

35. The catheter of claim 34, in which a groove is formed in said lower end of said catheter hub, said distal wall of said needle guard including a lower curved portion seated in said groove when said needle is in its said ready position.

36. The catheter of claim 35, in which said needle includes a slot formed in its periphery at a location proximal to the needle tip, said needle guard further including a transverse section extending between said proximal arm and said distal wall and including a flexible flap received in said needle slot when said needle guard is in its said blocking position.

37. The catheter of claim 35, in which said needle guard further comprises a proximal end wall having an opening for receiving said needle therethrough, said needle further comprising a large diameter on the needle shaft inward of said needle tip, the diameter of said large diameter segment being greater than that of said opening in said proximal end wall.

38. The catheter of claim 1, in which said needle guard includes first and second distal walls which overlap one another and form a distal barrier to said needle when said needle guard is in its said blocking position.

39. The catheter of claim 38, in which said needle guard further comprises a proximal end wall having an opening for receiving said needle therethrough and first and second arms extending respectively between said proximal end wall and said first and second distal walls.

40. The catheter of claim 39, in which said distal walls each include a curved protruding segment at the end of said arms, said catheter hub including an annular groove for receiving said protruding segments when said needle guard is in its said ready position.

41. The catheter of claim 40, in which each of said arms includes a wide section hingedly secured to said first and second distal walls and a narrow section extending from said wide section to said end wall.

42. The catheter of claim 41, in which said clamping means includes a clamping edge formed on a proximal end of said wide section.

43. The catheter of claim 42, in which said needle includes a large diameter segment on the needle shaft inward of said needle tip, the diameter of said large diameter segment being greater than that of said opening in said proximal end wall.

44. The catheter of claim 42, in which said needle guard includes a proximal end wall extending from said resilient portion and including an opening allowing said needle to pass therethrough, said needle further including a large diameter segment on the needle shaft inward of said needle tip, the diameter of said large diameter segment being greater than that of said opening in said proximal end wall.

45. The catheter of claim 44, in which said needle guard further comprises a proximal end wall having an opening for receiving said needle therethrough, said needle further comprising a large diameter on the needle shaft inward of said needle tip, the diameter of said large diameter segment being greater than that of said opening in said proximal end wall.

46. The catheter of claim 1, further comprising a wall extending distally and upwardly from the lower end of said proximal end wall and terminating at a clamping edge.

47. The catheter of claim 46, further comprising a resilient finger formed in said transverse arm, said finger and said clamping edge engaging opposing surfaces of said needle when said needle is in its said ready and blocking positions.

48. The catheter of claim 47, in which said needle includes a circumferential groove forced inwardly of said tip, said finger being adapted to enter into said groove in the event an axial force is applied to said needle in the proximal direction when said needle guard is in its said blocking position.

49. An IV catheter apparatus comprising a tubular catheter having a proximal end and a distal end, a needle having a needle shaft and a tip, said needle being received within said tubular catheter when in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, a unitary needle guard positioned in the interior of said catheter hub and including a resilient portion engaged by said needle shaft when said needle is in its said ready position, a section of said resilient portion of said needle guard being urged by said needle shaft into contact with an interior wall of said catheter hub when said needle is in its said ready position, and means formed on said interior wall of said catheter hub for engaging a segment of said needle guard for retaining said needle guard to said catheter hub during the movement of said needle between its said ready position and its said retracted position, said needle guard including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that contact between said section of said needle guard and said catheter hub is released.

50. The IV catheter apparatus of claim 49, in which said distal wall of said needle guard is contiguous with said resilient portion, said distal wall terminating at a curved lip engaging the underside of said needle shaft when said needle is in its said ready position.

51. The IV catheter apparatus of claim 50, further including a groove formed in said inner wall of said catheter hub, said groove engaging said needle guard in said ready position to aid in retaining said needle guard in said ready position.

52. The IV catheter apparatus of claim 51, in which a slot is formed in said needle shaft at a location proximal to said needle tip, said slot being positioned slightly distal of said contact point of said needle guard proximal arm so that, upon additional proximal axial movement of said needle, said contact point on said proximal arm of said needle guard is received in said needle slot.

53. The IV catheter apparatus of claim 52, further comprising a needle hub affixed to said proximal end of said needle and further comprising a tether attached at one end to said needle hub and at its other end to said needle guard.

54. The IV catheter apparatus of claim 52, in which said needle guard further includes an upper end proximal to said resilient portion and in contact with an opposed interior wall of the catheter hub when said needle is in its said ready position.

55. The IV catheter apparatus of claim 51, in which said needle guard further includes an upper end contiguous with said transverse segment and proximal to said resilient portion and in contact with an opposed interior wall of the catheter hub when said needle is in its said ready position.

56. The IV catheter apparatus of claim 50, further including a bump formed in said inner wall of said catheter hub, said bump engaging said needle guard in said ready position to aid in retaining said needle guard in said ready position.

57. The IV catheter apparatus of claim 56, in which a slot is formed in said needle shaft at a location proximal to said needle tip, said slot being positioned slightly distal of said contact point of said needle guard proximal arm so that, upon additional proximal axial movement of said needle, said contact point on said proximal arm of said needle guard is received in said needle slot.

58. The IV catheter apparatus of claim 57, further comprising a needle hub affixed to said proximal end of the needle and further comprising a tether attached at one end to said needle hub and at its other end to said needle guard.

59. The IV catheter apparatus of claim 58, further including a groove formed in said inner wall of said catheter hub, said groove engaging said needle guard in said ready position to aid in retaining said needle guard in said ready position.

60. The IV catheter apparatus of claim 59, in which a slot is formed in said needle shaft at a location proximal t said needle tip, said sot being positioned slightly distal of said contact point of said needle guard proximal arm so that, upon additional proximal axial movement of said needle, said contact point on said proximal arm of said needle guard is received in said needle slot.

61. The IV catheter apparatus of claim 59, further comprising a bump formed in said inner wall of said catheter hub, said bump engaging said needle guard in said ready position to aid in retaining said needle guard in said ready position.

62. The IV catheter apparatus of claim 59, in which said needle guard further includes an upper end contiguous with said transverse segment and proximal to said resilient portion and in contact with an opposed interior wall of the catheter hub when said needle is in its said ready position.

63. The IV catheter apparatus of claim 59, in which said needle guard further includes an upper end contiguous with said transverse segment and proximal to said resilient portion and in contact with an opposed interior wall of the catheter hub when said needle is in its said ready position.

64. The IV catheter apparatus of claim 56, in which said needle guard further includes an upper end contiguous with said transverse segment and proximal to said resilient portion and in contact with an opposed interior wall of the catheter hub when said needle is in its said ready position.

65. The IV catheter apparatus of claim 64, in which said needle guard includes a proximal end wall extending from said resilient portion and including an opening allowing said needle to pass therethrough, said needle further including a large diameter segment on the needle shaft inward of said needle tip, the diameter of said large diameter segment being greater than that of said opening in said proximal end wall.

66. The IV catheter apparatus of claim 50, further including a groove formed in said inner wall of said catheter hub, said groove engaging said needle guard in said ready position to aid in retaining said needle guard in said ready position.

67. The IV catheter apparatus of claim 66, in which said needle guard further includes an upper end proximal to said resilient portion and in contact with an opposed interior wall of the catheter hub when said needle is in its said ready position.

68. The IV catheter apparatus of claim 50, further comprising a bump formed in said inner wall of said catheter hub, said bump engaging said needle guard in said ready position to aid in retaining said needle guard in said ready position.

69. The IV catheter apparatus of claim 50, in which said needle guard further includes an upper end proximal to said resilient portion and in contact with an opposed interior wall of the catheter hub when said needle is in its said ready position.

70. The IV catheter apparatus of claim 49, in which a slot is formed in said needle shaft at a location proximal to said needle tip, said slot being positioned slightly distal of said contact point of said needle guard proximal arm so that, upon additional proximal axial movement of the needle, said contact point on said proximal arm of said needle guard is received in said needle slot.

71. The IV catheter apparatus of claim 70, further comprising a needle hub affixed to said proximal end of the needle and further comprising a tether attached at one end to said needle hub and at its other end to said needle guard.

72. The IV catheter apparatus of claim 70, in which said needle guard further includes an upper end proximal to said resilient portion and in contact with an opposed interior wall of the catheter hub when said needle is in its said ready position.

73. The IV catheter apparatus of claim 49, further including a groove formed in said inner wall of said catheter hub, said groove engaging said needle guard when said needle is in its said ready position to aid in retaining said needle guard in said retaining contact with said inner wall of said catheter hub while said needle moves from its said ready position to its said retracted position.

74. The IV catheter apparatus of claim 73, in which a slot is formed in said needle shaft at a location proximal to the needle tip, said slot being positioned slightly distal of said contact point of said needle guard proximal arm so that, upon additional proximal axial movement of said needle, said contact point on said proximal arm of said needle guard is received in said needle slot.

75. The IV catheter apparatus of claim 76, further comprising a needle hub affixed to said proximal end of the needle and further comprising a tether attached at one end to the needle hub and at its other end to said needle guard.

76. The IV catheter apparatus of claim 73, in which said needle guard further includes an upper end proximal to said resilient portion and in contact with an opposed interior wall of the catheter hub when said needle is in its said ready position.

77. The IV catheter apparatus of claim 49, further comprising a bump formed in said inner wall of said catheter hub, said bump engaging said needle guard in said ready position to aid in retaining said needle guard in said ready position.

78. The IV catheter apparatus of claim 49, in which said needle guard further includes an upper end proximal to said resilient portion and in contact with an opposed interior wall of the catheter hub in said ready position.

79. The IV catheter apparatus of claim 49, in which said needle guard further comprises a proximal arm having a lower curved segment in contact with an inner wall of said catheter hub when said needle is in its said ready position.

80. The IV catheter apparatus of claim 79, in which said proximal arm further includes an upper end in engagement with an opposed location of said inner wall of said catheter hub distal to the point of contact with said lower curved segment when said needle is in its said ready position.

81. The IV catheter apparatus of claim 80, in which a groove is formed in said lower end of said catheter hub, said distal wall of said needle guard including a lower curved portion seated in said groove when said needle is in its said ready position.

82. The IV catheter apparatus of claim 81, in which said needle includes a slot formed in its periphery at a location proximal to the needle tip, said needle guard further including a transverse section extending between said proximal arm and said distal wall and including a flexible flap received in said needle slot when said needle guard is in its said blocking position.

83. The IV catheter apparatus of claim 81, in which said needle guard further comprises a proximal end wall having an opening for receiving said needle therethrough, said needle further comprising a large diameter segment on the needle shaft inward of said needle tip, the diameter of said large diameter segment being greater than that of said opening in said proximal end wall.

84. The IV catheter apparatus of claim 83, in which said needle includes a circumferential groove forced inwardly of said tip, said finger being adapted to enter into said groove in the event an axial force is applied to said needle in the proximal direction when said needle guard is in its said blocking position.

85. The IV catheter apparatus of claim 49, in which said needle guard includes first and second distal walls which overlap one another and form a distal barrier to said needle when said needle guard is in its said blocking position.

86. The IV catheter apparatus of claim 85, in which said needle guard further comprises a proximal end wall having an opening for receiving said needle therethrough and first and second arms extending respectively between said proximal end wall and said first and second distal walls.

87. The IV catheter apparatus of claim 86, in which said distal walls each include a curved protruding segment at the end of said arms, said catheter hub including an annular groove for receiving said protruding segments when said needle guard is in its said ready position.

88. The IV catheter apparatus of claim 87, in which each of said arms includes a wide section hingedly secured to said first and second distal walls and a narrow section extending from said wide section to said end wall.

89. The IV catheter apparatus of claim 88, in which said needle guard includes a proximal end wall extending from said resilient portion and including an opening allowing said needle to pass therethrough, said needle further including a large diameter segment on the needle shaft inward of said needle tip, the diameter of said large diameter segment being greater than that of said opening in said proximal end wall.

90. The IV catheter apparatus of claim 89, in which said needle guard further comprises a proximal end wall having an opening for receiving said needle therethrough, said needle further comprising a large diameter segment on the needle shaft inward of said needle tip, the diameter of said large diameter segment being greater than that of said opening in said proximal end wall.

91. The IV catheter apparatus of claim 88, in which said needle includes a large diameter segment on the needle shaft inward of said needle tip, the diameter of said large diameter segment being greater than that of said opening in said proximal end wall.

92. An IV catheter apparatus comprising a tubular catheter having a proximal end and a distal end, a needle having a needle shaft and a tip, said needle being received within said tubular catheter when in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, a unitary needle guard positioned in the interior of said catheter hub and including a resilient portion engaged by said needle shaft when said needle is in its said ready position, a section of said resilient portion of said needle guard being urged by said needle shaft into contact with an interior wall of said catheter hub when said needle is in its said ready position, means formed on said interior wall of said catheter hub for engaging a segment of said needle guard for retaining said needle guard to said catheter hub during the movement of said needle between its said ready position and its said retracted position, said needle guard including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that retaining contact between said section of said needle guard and said catheter hub is released.

93. The IV catheter apparatus of claim 92, in which said distal wall of said needle guard is contiguous with said resilient portion, said resilient portion including a curved lip engaging the underside of said needle shaft when said needle is in its said ready position.

94. The IV catheter apparatus of claim 93, in which said retaining means includes a groove formed in said inner wall of said catheter hub, said groove receiving a portion of said needle guard when said needle is in its said ready position.

95. The IV catheter apparatus of claim 92, in which said retaining means includes a groove formed in said inner wall of said catheter hub, said groove receiving a portion of said needle guard when said needle is in its said ready position.

96. The IV catheter apparatus of claim 92, in which said needle guard further includes a transverse arm and a curved upper segment contiguous with said transverse arm and in contact with an opposed interior wall of the catheter hub when said needle is in its said ready position.

97. The IV catheter apparatus of claim 92, in which said needle guard further comprises a proximal wall having a lower curved segment in contact with said interior wall of said catheter hub when said needle is in its said ready position.

98. The IV catheter apparatus of claim 97, in which said proximal wall further includes an upper end in engagement with an opposed location of said interior wall of said catheter hub when said needle guard is in its said ready position.

99. The IV catheter apparatus of claim 98, in which said retaining means includes a groove formed in said interior wall of said catheter hub, said distal wall of said needle guard including a lower curved portion seated in said groove when said needle is in its said ready position.

100. The IV catheter apparatus of claim 92, in which said needle guard includes first and second distal walls which overlap one another and form a distal barrier to said needle when said needle guard is in its said blocking position.

101. The IV catheter apparatus of claim 100, in which each of said distal walls includes a curved lip engaging opposing surfaces of said needle shaft when said needle is in its said ready position.

102. The IV catheter apparatus of claim 101, in which said first and second distal walls each include a curved protruding segment, said retaining means including an annular groove formed in said catheter hub interior wall for receiving said protruding segments when said needle is in its said ready position.

103. The IV catheter apparatus of claim 102, in which said first and second distal walls each further include a wide section and a narrow section extending from said wide section toward said proximal end wall.

104. The IV catheter apparatus of claim 100, in which said needle guard further comprises a proximal end wall having an opening for receiving said needle therethrough and first and second arms extending respectively between said proximal end wall and said first and second distal walls.

105. The IV catheter apparatus of claim 104, in which said needle includes a large diameter segment on the needle shaft inward of said needle tip, the diameter of said large diameter segment being greater than that of said opening in said proximal end wall.

106. The IV catheter apparatus of claim 100, in which said first and second distal walls each include a curved protruding segment, said retaining means including an annular groove formed in said catheter hub interior wall for receiving said protruding segments when said needle is in its said ready position.

107. The IV catheter apparatus of claim 106, in which said first and second distal walls each further include a wide section and a narrow section extending from said wide section toward said proximal end wall.

108. An IV catheter apparatus comprising a tubular catheter having a proximal end and a distal end, a needle having a needle shaft and a tip, said needle being received within said tubular catheter when in a ready position, catheter hub attached to the proximal end of said catheter, said catheter hub having a hollow interior and an inner wall, said needle being movable between said ready position in which said tip is outside of said catheter hub and a retracted position in which said tip is within the interior of said catheter hub, and a unitary needle guard substantially positioned in the interior of said catheter hub and including a resilient portion engaged by said needle shaft when said needle is in said ready position, a section of said resilient portion of said needle guard being urged by said needle shaft into retaining contact with an interior wall of said catheter hub when said needle is in its said ready position, said needle guard also including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that said retaining contact between said section of said needle guard and said catheter hub is released upon the movement of said needle guard to its said blocking position.

109. The IV catheter apparatus of claim 108, in which said needle guard includes first and second distal walls which overlap one another and form a distal barrier to said needle when said needle guard is in its blocking position.

110. The IV catheter apparatus of claim 109, in which said first and second distal walls include a wide section and a narrow section extending from said wide section toward said proximal end wall.

111. The IV catheter apparatus of claim 110, in which said needle guard further comprises a proximal end wall having an opening for receiving said needle therethrough and first and second arms extending respectively between said proximal end wall and said first and second distal walls.

112. The IV catheter apparatus of claim 111, in which said needle includes a large diameter segment on the needle shaft inward of said needle tip, the diameter of said large diameter segment being greater than that of said opening in said proximal end wall.

\* \* \* \* \*